United States Patent
Weeber et al.

(10) Patent No.: US 11,629,127 B2
(45) Date of Patent: *Apr. 18, 2023

(54) DRUG-INDUCED ACTIVATION OF THE REELIN SIGNALING SYSTEM

(71) Applicant: UNIVERSITY OF SOUTH FLORIDA, Tampa, FL (US)

(72) Inventors: Edwin John Weeber, Apollo Beach, FL (US); Qingyou Li, Tampa, FL (US); Melinda Marie Peters, Riverview, FL (US); Hana Marie Soueidan, Wesley Chapel, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/723,140

(22) Filed: Apr. 18, 2022

(65) Prior Publication Data

US 2022/0324805 A1  Oct. 13, 2022

Related U.S. Application Data

(63) Continuation of application No. 16/758,991, filed as application No. PCT/US2018/057609 on Oct. 25, 2018, now Pat. No. 11,306,059.

(60) Provisional application No. 62/592,340, filed on Nov. 29, 2017, provisional application No. 62/577,072, filed on Oct. 25, 2017.

(51) Int. Cl.
  *C07C 233/88* (2006.01)
  *C07D 211/90* (2006.01)

(52) U.S. Cl.
  CPC .......... *C07D 211/90* (2013.01); *C07C 233/88* (2013.01)

(58) Field of Classification Search
  CPC .................. C07D 211/90; C07C 233/88
  See application file for complete search history.

(56) References Cited

U.S. PATENT DOCUMENTS

| 4,554,101 | A | 11/1985 | Hopp et al. |
| 5,580,859 | A | 12/1996 | Felgner et al. |
| 5,679,647 | A | 10/1997 | Carson et al. |
| 5,703,055 | A | 12/1997 | Felgner et al. |
| 6,323,177 | B1 | 11/2001 | Curran et al. |
| 7,582,657 | B2 | 9/2009 | Chen et al. |
| 9,241,975 | B2 | 1/2016 | Weeber et al. |
| 9,718,803 | B2 | 8/2017 | Allen et al. |
| 11,306,059 | B2 * | 4/2022 | Weeber ............... A61K 31/167 |
| 2003/0165485 | A1 | 9/2003 | Bertilsson et al. |
| 2009/0215896 | A1 | 8/2009 | Morseman et al. |
| 2012/0058109 | A1 | 3/2012 | Weeber et al. |
| 2016/0271213 | A1 | 9/2016 | Weeber et al. |

FOREIGN PATENT DOCUMENTS

WO  2016073633  5/2016

OTHER PUBLICATIONS

Strasser, et al., Receptor Clustering Is Involved in Reelin Signaling, Molecular and Cellular Biology, Feb. 2004, p. 1378-1386.
Yang, et al., Activated protein C ligation of ApoER2 (LRP8) causes Dab1-dependent signaling in U937 cells, PNAS 2009, 274-279.
Pubchem CID792446 ST50929554 accessed Sep. 18, 2017. Available on-line at: https://pubchem.ncbi.nlm.nih.gov/compound/792446#section=Top.
Heagerty, Patrick J., Thomas Lumley, and Margaret S. Pepe. "Time-dependent ROC curves for censored survival data and a diagnostic marker." Biometrics 56.2 (2000): 337-344.
Kyte, Jack, and Russell F. Doolittle. "A simple method for displaying the hydropathic character of a protein." Journal of molecular biology 157.1 (1982): 105-132.
Donnelly, John J., et al. "DNA vaccines." Annual review of immunology 15.1 (1997): 617-648.
IUPAC 1974 Recommendations for Section E. Rules for the Nomenclature of Organic Chemistry. Fundamental Stereochemistry, 1976, 13-30.
C.T.F.A. Cosmetic Ingredient Handbook, 1992, pp. 587-592.
Remington's Pharmaceutical Sciences, 15th Ed. 1975, pp. 335-337.
McCutcheon's vol. 1, Emulsifiers & Detergents, 1994, North American Edition, pp. 236-239.
International Preliminary Report on Patentability issued for Application No. PCT/US2018/057609, dated May 7, 2020.
International Search Report and Written Opinion in PCT/US2018/057609, dated Feb. 19, 2019. 12 pages.
Extended European Search Report issued for U.S. Appl. No. 18/870,264, dated Jul. 6, 2021.
Saeed, Aamer, et al. "Synthesis, cytotoxicity and molecular modelling studies of new phenylcinnamide derivatives as potent inhibitors of cholinesterases." European journal of medicinal chemistry 78 (2014): 43-53.
Carradori, Simone, and Romano Silvestri. "New frontiers in selective human MAO-B inhibitors: miniperspective." Journal of medicinal chemistry 58.17 (2015): 6717-6732.

\* cited by examiner

*Primary Examiner* — Timothy R Rozof
(74) *Attorney, Agent, or Firm* — Meunier Carlin & Curfman LLC

(57) ABSTRACT

Disclosed herein are compounds for activating the Reelin signaling system for the treatment of neurological disorders Further provided are compounds and methods for activating a lipoprotein receptor, such as ApoER2 or VLDLR.

15 Claims, 20 Drawing Sheets

Proteins and associated psychocognitive disorders

Reelin — Schizophrenia, Lissencephaly

ApoE — Alzheimer's disease

NF1 — Neurofibromatosis

CBP — Rubinstein–Taybi syndrome

Secretin — Autism

Ube3a — Angelman syndrome

DRUG-INDUCED ACTIVATION OF THE REELIN SIGNALING SYSTEM

CROSS-REFERENCE TO RELATED APPLICATIONS

This application is a continuation of U.S. application Ser. No. 16/758,991, filed on Apr. 24, 2020, which is a National Phase Application of PCT/US2018/057609, filed on Oct. 25, 2018, which claims priority to U.S. Provisional Patent Application No. 62/577,072 filed Oct. 25, 2017, and U.S. Provisional Patent Application No. 62/592,340 filed Nov. 29, 2017, each of which is incorporated herein by reference in its entirety.

FIELD

This disclosure relates to compounds for activating the Reelin signaling system for the treatment of neurological disorders.

INTRODUCTION

Activation of Apolipoprotein receptor 2 (ApoER2) and the very-low density lipoprotein receptor (VLDLR) are involved in a myriad of neuronal activities in both the developing and adult central nervous system. These receptors are activated through the binding and internalization of the Reelin protein. The mode of action for this receptor activation is through dimerization or clustering of ApoER2 or VLDLR, which leads to the phosphorylation and activation of the intracellular adapter protein Dab1.

Reelin is expressed in the brain and in peripheral tissues. The lack of Reelin expression is associated with neurological disorders and inability of organs to self-repair. Administering Reelin as a therapeutic in its endogenous absence is problematic due to its size. Full-length Reelin is a 450 kDa protein that is cleaved to smaller protein fragments. The 180 kDa protein fragment may be the major fragment that activates the Reelin signaling system, but it is too large to pass the blood-brain-barrier (BBB). Soluble small molecules that can easily pass the BBB and have the same mechanism of action as Reelin could be more readily developed as a therapeutic. There is a need for small molecule agonist compounds that can be used in place of Reelin to activate the Reelin signaling system.

SUMMARY

In an aspect, the disclosure relates to methods of treating a disease or disorder in a subject in need thereof, the method comprising administering to the subject an agonist of a lipoprotein receptor.

In a further aspect, the disclosure relates to methods of improving cognitive function in a subject in need thereof, the method comprising administering to the subject an agonist of a lipoprotein receptor.

Another aspect of the disclosure provides methods of increasing dendritic spine density in a subject in need thereof, the method comprising administering to the subject an agonist of a lipoprotein receptor.

Another aspect of the disclosure provides methods of improving associative learning in a subject in need thereof, the method comprising administering to the subject an agonist of a lipoprotein receptor.

Another aspect of the disclosure provides methods of improving spatial learning in a subject in need thereof, the method comprising administering to the subject an agonist of a lipoprotein receptor.

Another aspect of the disclosure provides methods of improving long-term potentiation of neurons in a subject in need thereof, the method comprising administering to the subject an agonist of a lipoprotein receptor.

In some embodiments, the lipoprotein receptor is selected from ApoER2 and VLDLR. In some embodiments, the disease or disorder is of the central nervous system. In some embodiments, the disease or disorder is a developmental disorder, a cognitive disorder, a degenerative disorder, a neuropsychiatric disorder, or brain injury. In some embodiments, the developmental disorder is Lissecephaly. In some embodiments, the cognitive disorder is selected from Angelman Syndrome and schizophrenia. In some embodiments, the degenerative disorder is Alzheimer's disease. In some embodiments, the neuropsychiatric disorder is selected from schizophrenia and bipolar disorder. In some embodiments, the brain injury is traumatic brain injury (TBI). In some embodiments, the disease or disorder is selected from Lissecephaly, fragile X syndrome, William's syndrome, Rett syndrome, Down's syndrome, Angelman syndrome, autism, ischemia, hypoxia, Alzheimer's disease, Reelin deficiency, schizophrenia, bipolar disorder, neurodegeneration, traumatic brain injury, mental retardation, dementia, bipolar disorder, and stroke.

Another aspect of the disclosure provides methods of treating a central nervous system disease or disorder by activating the Reelin signaling system in a subject in need thereof, the method comprising administering to the subject an effective amount of a small molecule agonist of a lipoprotein receptor.

In some embodiments, the agonist comprises a compound according to Formula

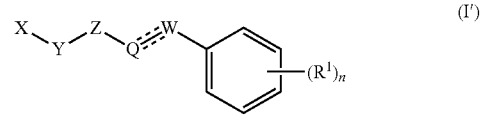

(I')

or a pharmaceutically acceptable salt thereof, wherein each $R^1$ is independently hydrogen, halogen, hydroxyl, alkoxyl, or alkyl; n is an integer from 0 to 5; W is C, CH, $CH_2$, or O; Q is C, CH, $CH_2$, N, or NH; Z is C=O, NH, or $CH_2$; Y is C=O, NH, or $CH_2$, or Z and Y may together form a bicyclic ring; and X is cycloalkyl, cycloalkenyl, cycloalkynyl, heterocyclyl, aryl, or heteroaryl, and may be unsubstituted or substituted with $(R^2)_m$, wherein each $R^2$ is independently hydrogen, halogen, hydroxyl, alkoxyl, or alkyl, and m is an integer from 0 to 5;

or Formula I:

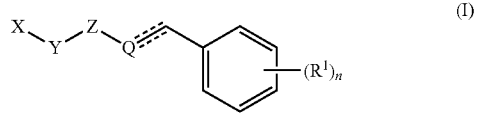

(I)

or a pharmaceutically acceptable salt thereof, wherein each $R^1$ is independently hydrogen, halogen, hydroxyl, alkoxyl, or alkyl; n is an integer from 0 to 5; Q is C, CH, $CH_2$, N, or NH, Z is C=O, NH, or $CH_2$; Y is C=O, NH, or $CH_2$, or Z and Y may together form a bicyclic ring; and X is cycloakyl, cycloalkenyl, cycloalkynyl, heterocyclyl, aryl, or heteroaryl, and may be unsubstituted or substituted with $(R^2)_m$, wherein each $R^2$ is independently hydrogen, halogen, hydroxyl, alkoxyl, or alkyl, and m is an integer from 0 to 5;

or Formula II:

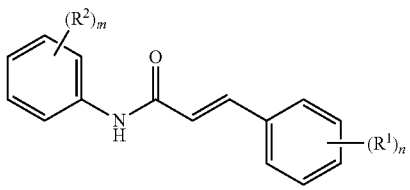

or a pharmaceutically acceptable salt thereof, wherein each $R^1$ is independently hydrogen, halogen, hydroxyl, alkoxyl, or alkyl; n is an integer from 0 to 5; each $R^2$ is independently hydrogen, halogen, hydroxyl, alkoxyl, or alkyl; and m is an integer from 0 to 5;

or Formula III:

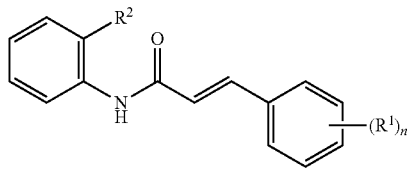

or a pharmaceutically acceptable salt thereof, wherein each $R^1$ is independently hydrogen, halogen, hydroxyl, alkoxyl, or alkyl; n is an integer from 0 to 5; and $R^2$ is hydrogen, halogen, hydroxyl, alkoxyl, or alkyl.

Another aspect of the disclosure provides methods of activating a lipoprotein receptor in a subject in need thereof, the method comprising administering to the subject a compound according to Formula I':

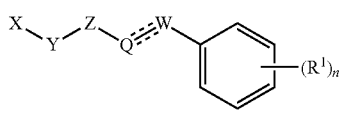

or a pharmaceutically acceptable salt thereof, wherein each $R^1$ is independently hydrogen, halogen, hydroxyl, alkoxyl, or alkyl; n is an integer from 0 to 5; W is C, CH, $CH_2$, or O; is C, CH, $CH_2$, N, or NH; Z is C=O, NH, or $CH_2$; Y is C=O, NH, or $CH_2$, or Z and Y may together form a bicyclic ring, and X is cycloalkyl, cycloalkenyl, cycloalkynyl, heterocyclyl, aryl, or heteroaryl, and may be unsubstituted or substituted with $(R^2)_m$, wherein each $R^2$ is independently hydrogen, halogen, hydroxyl, alkoxyl, or alkyl, and m is an integer from 0 to 5;

or Formula I'.

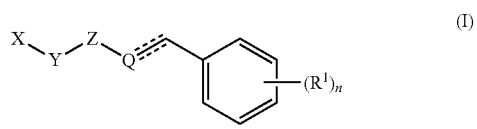

or a pharmaceutically acceptable salt thereof, wherein each $R^1$ is independently hydrogen, halogen, hydroxyl, alkoxyl, or alkyl; n is an integer from 0 to 5; Q is C, CH, $CH_2$, N, or NH; Z is C=O, NH, or $CH_2$; Y is C=O, NH, or $CH_2$, or Z and Y may together form a bicyclic ring; and X is cycloalkyl, cycloalkenyl, cycloalkynyl, heterocyclyl, aryl, or heteroaryl, and may be unsubstituted or substituted with $(R^2)_m$, wherein each $R^2$ is independently hydrogen, halogen, hydroxyl, alkoxyl, or alkyl, and m is an integer from 0 to 5;

or Formula II;

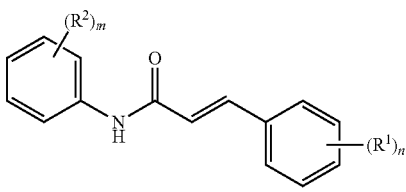

or a pharmaceutically acceptable salt thereof; wherein each $R^1$ is independently hydrogen, halogen, hydroxyl, alkoxyl, or alkyl; n is an integer from 0 to 5; each $R^2$ is independently hydrogen, halogen, hydroxyl, alkoxyl, or alkyl; and m is an integer from 0 to 5;

or Formula III:

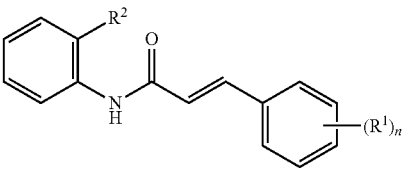

or a pharmaceutically acceptable salt thereof, wherein each $R^1$ is independently hydrogen, halogen, hydroxyl, alkoxyl, or alkyl; n is an integer from 0 to 5, and $R^2$ is hydrogen, halogen, hydroxyl, alkoxyl, or alkyl. In some embodiments, the lipoprotein receptor is selected from ApoER2 and VLDLR.

Another aspect of the disclosure provides an agonist of ApoER2 or VLDLR, wherein the agonist is a compound according to Formula I'.

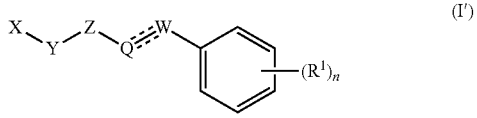

or a pharmaceutically acceptable salt thereof, wherein each $R^1$ is independently hydrogen, halogen, hydroxyl, alkoxyl, or alkyl; n is an integer from 0 to 5; W is C, CH, $CH_2$, or O, Q is C, CH, $CH_2$, N, or NH; Z is C=O, NH, or $CH_2$; Y is C=O, NH, or $CH_2$, or Z and Y may together form a bicyclic ring; and X is cycloalkyl, cycloalkenyl, cycloalkynyl, heterocyclyl, aryl, or heteroaryl, and may be unsubstituted or substituted with $(R^2)_m$, wherein each $R^2$ is independently hydrogen, halogen, hydroxyl, alkoxyl, or alkyl, and m is an integer from 0 to 5;
or Formula I.

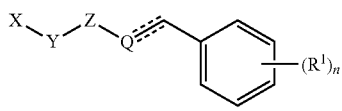

or a pharmaceutically acceptable salt thereof, wherein each $R^1$ is independently hydrogen, halogen, hydroxyl, alkoxyl, or alkyl; n is an integer from 0 to 5; Q is C, CH, $CH_2$, N, or NH; Z is C=O, NH, or $CH_2$; Y is C=O, NH, or $CH_2$, or Z and Y may together form a bicyclic ring; and X is cycloalkyl, cycloalkenyl, cycloakynyl, heterocyclyl, aryl, or heteroaryl, and may be unsubstituted or substituted with $(R^2)_m$, wherein each $R^2$ is independently hydrogen, halogen, hydroxyl, alkoxyl, or alkyl, and m is an integer from 0 to 5;
or Formula II:

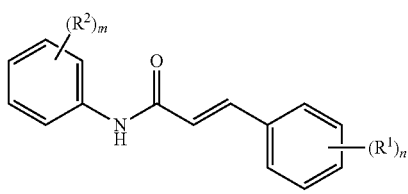

or a pharmaceutically acceptable salt thereof, wherein each $R^1$ is independently hydrogen, halogen, hydroxyl, alkoxyl, or alkyl; n is an integer from 0 to 5; each $R^2$ is independently hydrogen, halogen, hydroxyl, alkoxyl, or alkyl; and m is an integer from 0 to 5;
or Formula III:

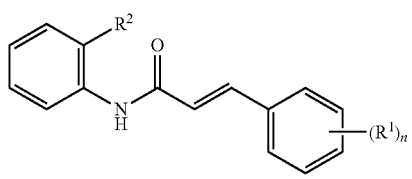

or a pharmaceutically acceptable salt thereof, wherein each $R^1$ is independently hydrogen, halogen, hydroxyl, alkoxyl, or alkyl; n is an integer from 0 to 5; and $R^2$ is hydrogen, halogen, hydroxyl, alkoxyl, or alkyl Another aspect of the disclosure provides a compound according to Formula I'.

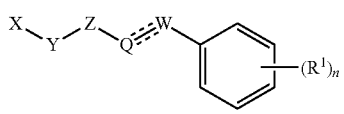

or a pharmaceutically acceptable salt thereof, wherein each $R^1$ is independently hydrogen, halogen, hydroxyl, alkoxyl, or alkyl; n is an integer from 0 to 5; W is C, CH, $CH_2$, or O; Q is C, CH, $CH_2$, N, or NH; Z is C=O, NH, or $CH_2$; Y is C=O, NH, or $CH_2$, or Z and Y may together form a bicyclic ring; and X is cycloalkyl, cycloalkenyl, cycloalkynyl, heterocyclyl, aryl, or heteroaryl, and may be unsubstituted or substituted with $(R^2)_m$, wherein each R is independently hydrogen, halogen, hydroxyl, alkoxyl, or alkyl, and m is an integer from 0 to 5;
or Formula I.

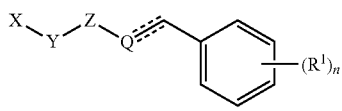

or a pharmaceutically acceptable salt thereof, wherein each $R^1$ is independently hydrogen, halogen, hydroxyl, alkoxyl, or alkyl; n is an integer from 0 to 5; Q is C, CH, $CH_2$, N, or NH; Z is C=O, NH, or $CH_2$; Y is C=O, NH, or $CH_2$, or Z and Y may together form a bicyclic ring; and X is cycloakyl, cycloalkenyl, cycloalkynyl, heterocyclyl, aryl, or heteroaryl, and may be unsubstituted or substituted with $(R^2)_m$, wherein each $R^2$ is independently hydrogen, halogen, hydroxyl, alkoxyl, or alkyl, and m is an integer from 0 to 5;
or Formula II:

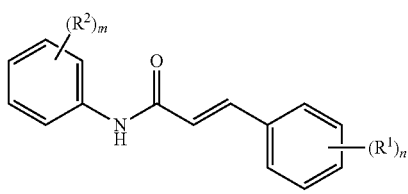

or a pharmaceutically acceptable salt thereof, wherein each $R^1$ is independently hydrogen, halogen, hydroxyl, alkoxyl, or alkyl; n is an integer from 0 to 5; each $R^2$ is independently hydrogen halogen, hydroxyl, alkoxyl, or alkyl; and m is an integer from 0 to 5;
or Formula III,

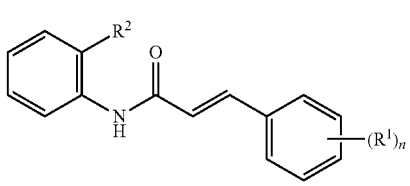

or a pharmaceutically acceptable salt thereof, wherein each $R^1$ is independently hydrogen, halogen, hydroxyl, alkoxyl, or alkyl; n is an integer from 0 to 5; and $R^2$ is hydrogen, halogen, hydroxyl, alkoxyl, or alkyl.

Another aspect of the disclosure provides a pharmaceutical composition comprising a compound as detailed herein. In some embodiments, the composition further comprises a carrier for oral, intranasal, intravaginal, transdermal, intravenous, intraarterial, intratumoral, intraperitoneal, or topical administration.

In some embodiments, the agonist or compound is of Formula I', and $R^1$ is methoxy, OH, or isopropyl. In some embodiments, the agonist or compound is of Formula I', and Z and Y together form a heteroaryl ring. In some embodiments, the agonist or compound is of Formula I', and Z and Y together form benzimidazole. In some embodiments, the agonist or compound is of Formula I', and X is phenyl substituted with $(R^2)_m$. In some embodiments, at least one $R^2$ is methyl. In some embodiments, at least one $R^2$ is Cl or I. In some embodiments, the agonist or compound is of Formula I, and $R^1$ is methoxy, OH, or isopropyl. In some embodiments, the agonist or compound is of Formula I, and Z and Y together form a heteroaryl ring. In some embodiments, the agonist or compound is of Formula I, and Z and Y together form benzimidazole. In some embodiments, the agonist or compound is of Formula I, and X is phenyl substituted with $(R^2)_m$. In some embodiments, at least one $R^2$ is methyl. In some embodiments, at least one $R^2$ is Cl or I. In some embodiments, the agonist or compound is of Formula II, and $R^1$ is $C_{1-4}$ alkyl. In some embodiments, $R^1$ is methyl, ethyl, or isopropyl. In some embodiments, the agonist or compound is of Formula II, and $R^2$ is Cl or I. In some embodiments, the agonist or compound is of Formula I', and $R^1$ is Cl, n is 2, W is, Q is $CH_2$ Z is C=O, Y is NH, and X is phenyl substituted with $(R^2)_m$, wherein $R^2$ is Cl and m is 1 In some embodiments, the agonist or compound is of Formula III, and $R^1$ is methyl, ethyl, or isopropyl. In some embodiments, the agonist or compound is of Formula III, and $R^1$ is isopropyl. In some embodiments, n is 1 or 2. In some embodiments, the agonist or compound is of Formula III, and $R^2$ is Cl. In some embodiments, the agonist or compound is of Formula III, and $R^2$ is Cl, $R^1$ is isopropyl, and n is 1. In some embodiments, the agonist or compound is selected from the following:

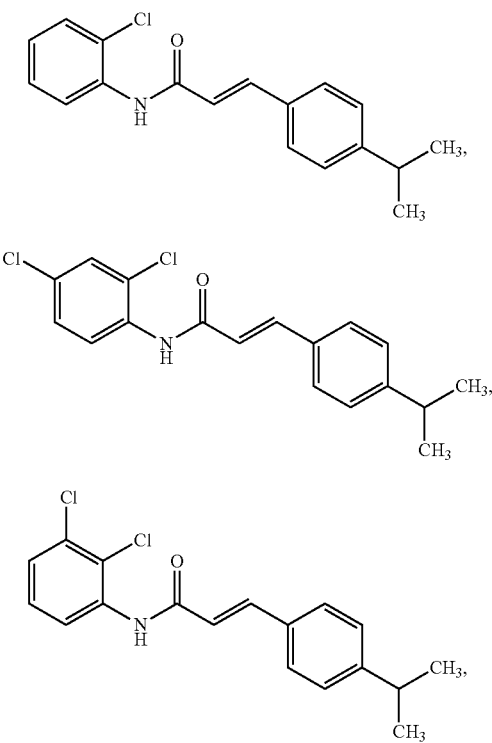

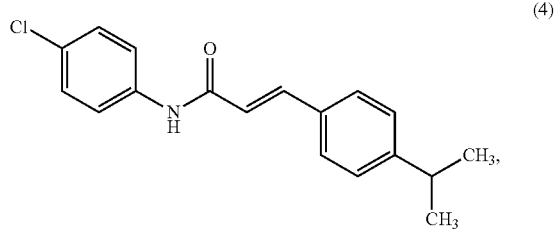

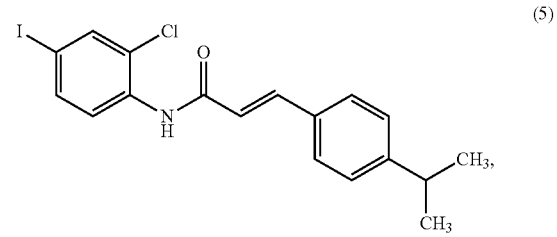

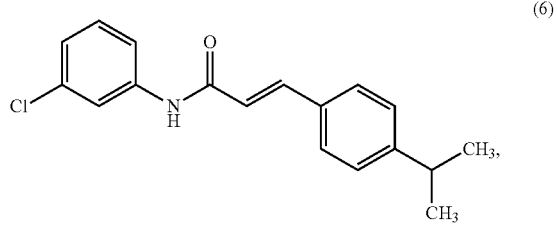

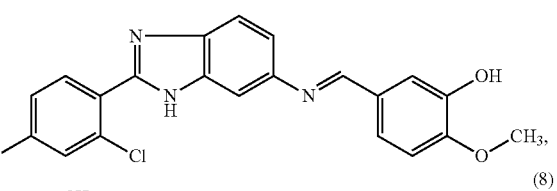

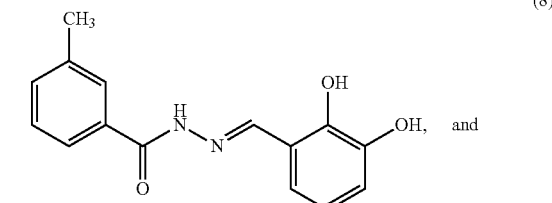

or a pharmaceutically acceptable salt thereof.

The disclosure provides for other aspects and embodiments that will be apparent in light of the following detailed description and accompanying figures.

DETAILED DESCRIPTION

Figure 1A:
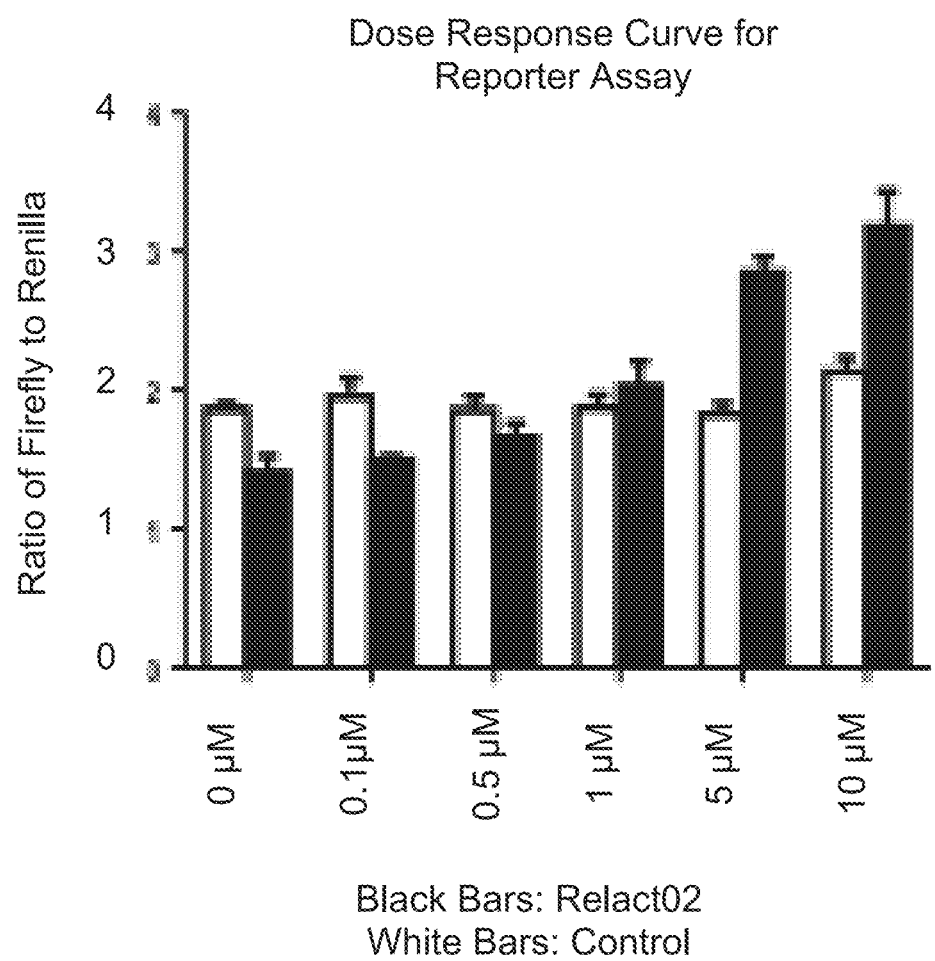
FIG. 1A is a close response curve for assessing luciferase activity to examine ApoER2 dimerization.

Described herein are compounds for activating a Reelin signaling pathway and methods of administering the compounds for treating a disease or disorder. Reelin signaling disruption is a factor in a variety of neurological and neurodegenerative disorders. The compounds detailed herein are agonists that may act upon the lipoprotein receptor system in a manner similar to Reelin for use as therapeutics in the improvement of cognitive function as well as the treatment of neurological and neurodegenerative disorders. The compounds may be administered to a subject for the treatment of a variety of disorders of the central nervous system and improving cognitive function

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and," and "the" include plural references unless the context clearly dictates otherwise. The present disclosure also contemplates other embodiments "comprising," "consisting of," and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The term "about" as used herein as applied to one or more values of interest, refers to a value that is similar to a stated reference value. In certain aspects, the term 'about' refers to a range of values that fall within 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 7$^{th}$ Edition, John Wiley & Sons, Inc. New York, 2013; Larock, *Comprehensive Organic Transformations*, VCH Publishers, Inc. New York, 1989; Carruthers, *Some Modern Methods of Organic Synthesis*, 3$^{rd}$ Edition, Cambridge University Press, Cambridge, 1987; the entire contents of each of which are incorporated herein by reference.

The term "alkoxy" or "alkoxyl" as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy and tert-butoxy.

The term "alkyl" as used herein, means a straight or branched, saturated hydrocarbon chain containing from 1 to 20 carbon atoms. The term "lower alkyl" or "$C_{1-6}$ alkyl" means a straight or branched chain hydrocarbon containing from 1 to 6 carbon atoms. The term "$C_{1-4}$ alkyl" means a straight or branched chain hydrocarbon containing from 1 to 4 carbon atoms. The term "$C_{1-3}$ alkyl" means a straight or branched chain hydrocarbon containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkenyl" as used herein, means an unsaturated hydrocarbon chain containing from 2 to 20 carbon atoms and at least one carbon-carbon double bond.

The term "alkynyl" as used herein, means an unsaturated hydrocarbon chain containing from 2 to 20 carbon atoms and at least one carbon-carbon triple bond.

The term "alkoxyalkyl" as used herein, refers to an alkoxy group, as defined herein, appended to the parent molecular moiety through an alkylene group, as defined herein.

The term "arylalkyl" as used herein, refers to an aryl group, as defined herein, appended to the parent molecular moiety through an alkylene group, as defined herein.

The term "alkylamino," as used herein, means at least one alkyl group, as defined herein, is appended to the parent molecular moiety through an amino group, as defined herein.

The term "alkylene" as used herein, refers to a divalent group derived from a straight or branched chain hydrocarbon of 1 to 10 carbon atoms, for example, of 2 to 5 carbon atoms. Representative examples of alkylene include, but are not limited to, —$CH_2CH_2$—, —$CH_2CH_2CH_3$—, —$CH_2CH_2CH_2CH_2$—, and —$CH_2CH_2CH_2CH_2CH_2$—.

The term "amide." as used herein, means —C(O)NR— or —NRC(O)—, wherein R may be hydrogen, alkyl, cycloalkyl, aryl, heteroaryl, heterocycle, alkenyl, or heteroalkyl.

The term "aminoalkyl," as used herein, means at least one amino group, as defined herein, is appended to the parent molecular moiety through an alkylene group, as defined herein.

The term "amino" as used herein, means —$NR_xR_y$, wherein $R_x$ and $R_y$ may be hydrogen, alkyl, cycloalkyl, aryl, heteroaryl, heterocycle, alkenyl, or heteroalkyl. In the case of an aminoalkyl group or any other moiety where amino appends together two other moieties, amino may be —$NR_x$—, wherein $R_x$ may be hydrogen, alkyl, cycloalkyl, aryl, heteroaryl, heterocycle, alkenyl, or heteroalkyl.

The term "aryl" as used herein, refers to an aromatic group such as a phenyl group, or a bicyclic fused ring system. Bicyclic fused ring systems are exemplified by a phenyl group appended to the parent molecular moiety and fused to a cycloalkyl group, as defined herein, a phenyl group, a heteroaryl group, as defined herein, or a heterocycle, as defined herein. Representative examples of aryl include, but are not limited to, indolyl, naphthyl, phenyl, quinolinyl, and tetrahydroquinolinyl.

The term "carboxyl" as used herein, means a carboxylic acid, or —COOH.

The term "cycloalkyl" means a monovalent saturated hydrocarbon ring or a bicyclic group. Cycloalkyl groups have zero heteroatoms and zero double bonds. Cycloalkyl groups are monocyclic, or are fused, spiro, or bridged bicyclic ring systems. Monocyclic cycloalkyl groups contain 3 to 10 carbon atoms, preferably 4 to 7 carbon atoms, and more preferably 5 to 6 carbon atoms in the ring. Bicyclic cycloalkyl groups contain 8 to 12 carbon atoms, preferably 9 to 10 carbon atoms in the ring. Cycloalkyl groups may be substituted or unsubstituted. Cycloalkyl groups include, for example, cyclopropyl, cyclobutyl, cyclopentyl, cyclohexyl, and cycloheptyl.

The term "cycloalkenyl," as used herein, means a non-aromatic monocyclic or multicyclic ring system containing at least one carbon-carbon double bond and preferably having from 5-10 carbon atoms per ring. Exemplary monocyclic cycloalkenyl rings include cyclopentenyl, cyclohexenyl, and cycloheptenyl.

The term "cycloalkynyl," as used herein, means a monocyclic or multicyclic ring system containing at least one carbon-carbon triple bond and preferably having from 5-10 carbon atoms per ring or more than 10 carbon atoms per ring.

The term "haloalkyl" as used herein, means an alkyl group, as defined herein, in which one, two, three, four, five, six, seven or eight hydrogen atoms are replaced by a halogen. Representative examples of haloalkyl include, but are not limited to, 2-fluoroethyl, 2,2,2-trifluoroethyl, trifluoromethyl, difluoromethyl, pentafluoroethyl, and trifluoropropyl such as 3,3,3-trifluoropropyl.

The term 'halogen' or 'halo' as used herein, means Cl, Br, I, or F.

The term "heteroalkyl" as used herein, means an alkyl group, as defined herein, in which at least one of the carbons of the alkyl group is replaced with a heteroatom, such as oxygen, nitrogen, and sulfur. Representative examples of heteroalkyls include, but are not limited to, alkyl ethers, secondary and tertiary alkyl amines, amides, and alkyl sulfides.

The term "heteroaryl" as used herein, refers to an aromatic monocyclic ring or an aromatic bicyclic ring system containing at least one heteroatom independently selected from the group consisting of N, O, and S. The aromatic monocyclic rings are five or six membered rings containing at least one heteroatom independently selected from the group consisting of N, O, and S. The five membered aromatic monocyclic rings have two double bonds and the six membered six membered aromatic monocyclic rings have three double bonds. The bicyclic heteroaryl groups are exemplified by a monocyclic heteroaryl ring appended to the parent molecular moiety and fused to a monocyclic cycloalkyl group, as defined herein, a monocyclic aryl group, as defined herein, a monocyclic heteroaryl group, as defined herein, or a monocyclic heterocycle, as defined herein. Representative examples of heteroaryl include, but are not limited to, indolyl, pyridinyl (including pyridin-2-yl, pyridin-3-yl, pyrindin-4-yl), pyrimidinyl, pyrazinyl, pyridazinyl, pyrazolyl, pyrrolyl, benzopyrazolyl, 1,2,3-triazolyl, 1,3,4-thiadiazolyl, 1,2,4-thiadiazoyl, 1,3,4-oxadiazolyl, 1,2,4-oxadiazolyl, imidazolyl, thiazolyl, isothiazolyl, thienyl, benzimidazolyl, benzothiazolyl, benzoxazolyl, benzoxadiazolyl, benzothienyl, benzofuranyl, isobenzofuranyl, furanyl, oxazolyl, isoxazolyl, purinyl, isoindolyl, quinoxalinyl, indazolyl, quinazolinyl, 1,2,4-triazinyl, 1,3,5-triazinyl, isoquinolinyl, quinolinyl, 6,7-dihydro-1,3-benzothiazolyl, imidazo[1,2-a]pyridinyl, naphthyridinyl, pyridoimidazolyl, thiazolo[5,4-b]pyridin-2-yl, thiazolo[5,4-d]pyrimidin-2-yl.

The term "heterocycle" or "heterocyclic" or "heterocycyl" as used herein means a monocyclic heterocycle, a bicyclic heterocycle (heterobicyclic), or a tricyclic heterocycle. The monocyclic heterocycle is a three-, four-, five-, six-, seven-, or eight-membered ring containing at least one heteroatom independently selected from the group consisting of O. N, and S. The three- or four-membered ring contains zero or one double bond, and one heteroatom selected from the group consisting of O, N, and S. The five-membered ring contains zero or one double bond and one, two, or three heteroatoms selected from the group consisting of O, N, and S. The six-membered ring contains zero, one, or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazoidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, azabicyclo[2.2.1]heptyl (including 2-azabicyclo[2.2.1]hept-2-yl), 2,3-dihydro-1H-indoyl, isoindolinyl, octahydrocyclopenta[c]pyrrolyl, octahydropyrrolopyridinyl, and tetrahydroisoquinolinyl, Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms Examples of tricyclic heterocycles include, but not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1$^{3,7}$] decane), and oxa-adamantane (2-oxatricyclo[3.3.1.1$^{3,7}$] decane). The monocyclic, bicyclic, and tricyclic heterocycles are connected to the parent molecular moiety through any carbon atom or any nitrogen atom contained within the rings, and can be unsubstituted or substituted.

The term "heteroarylalkyl" as used herein, refers to a heteroaryl group, as defined herein, appended to the parent molecular moiety through an alkylene group, as defined herein.

The term "heterocyclylalkyl" as used herein, refers to a heterocycle group, as defined herein, appended to the parent molecular moiety through an alkylene group, as defined herein.

The term "hydroxyl" or "hydroxy" as used herein, means an —OH group.

The term "hydroxyalkyl" as used herein, means at least one —OH group, is appended to the parent molecular moiety through an alkylene group, as defined herein.

In some instances, the number of carbon atoms in a hydrocarbyl substituent (e.g., alkyl or cycloalkyl) is indicated by the prefix "—C$_x$—$_y$—", wherein x is the minimum and y is the maximum number of carbon atoms in the substituent. Thus, for example, "C$_{1-3}$ alkyl" refers to an alkyl substituent containing from 1 to 3 carbon atoms.

The term "substituted" refers to a group that may be further substituted with one or more non-hydrogen substituent groups. Substituent groups include, but are not limited to, halogen, =O (oxo), =S (thioxo), cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl —COOH, ketone, amide, carbamate, and acyl.

The term " ⋯⋯ " designates a single bond (—) or a double bond (═) or a triple bond (≡).

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

"Amino acid" as used herein refers to naturally occurring and non-natural synthetic amino acids, as well as amino acid analogs and amino acid mimetics that function in a manner similar to the naturally occurring amino acids. Naturally occurring amino acids are those encoded by the genetic code. Amino acids can be referred to herein by either their commonly known three-letter symbols or by the one-letter symbols recommended by the IUPAC-IUB Biochemical Nomenclature Commission. Amino acids include the side chain and polypeptide backbone portions.

The term "antagonist" refers to a molecule which blocks (e.g., reduces or prevents) a biological activity.

As used herein, the term "agonist" refers to a molecule or compound that triggers (e.g., initiates or promotes), partially or fully enhances, stimulates, or activates one or more biological activities. An agonist may mimic the action of a naturally occurring substance. In some embodiments, an agonist as detailed herein may mimic the action of Reelin. In some embodiments, the term refers to a compound that activates the Reelin signaling system. Whereas an agonist causes an action, an antagonist blocks the action of the agonist.

The terms "control," "reference level," and "reference" are used herein interchangeably. The reference level may be a predetermined value or range, which is employed as a benchmark against which to assess the measured result. "Control group" as used herein refers to a group of control subjects. The predetermined level may be a cutoff value from a control group. The predetermined level may be an average from a control group. Cutoff values (or predetermined cutoff values) may be determined by Adaptive Index Model (AIM) methodology. Cutoff values (or predetermined cutoff values) may be determined by a receiver operating curve (ROC) analysis from biological samples of the patient group. ROC analysis, as generally known in the biological arts, is a determination of the ability of a test to discriminate one condition from another, e.g., to determine the performance of each marker in identifying a patient having CRC. A description of ROC analysis is provided in P. J. Heagerty at al. (*Biometrics* 2000, 56, 337-44), the disclosure of which is hereby incorporated by reference in its entirety. Alternatively, cutoff values may be determined by a quartile analysis of biological samples of a patient group. For example, a cutoff value may be determined by selecting a value that corresponds to any value in the 25th-75th percentile range, preferably a value that corresponds to the 25th percentile, the 50th percentile or the 75th percentile, and more preferably the 75th percentile. Such statistical analyses may be performed using any method known in the art and can be implemented through any number of commercially available software packages (e.g., from Analyse-it Software Ltd., Leeds, U K; StataCorp LP, College Station. Tex.; SAS Institute Inc., Cary, N.C.). The healthy or normal levels or ranges for a target or for a protein activity may be defined in accordance with standard practice. A control may be an subject or cell without an agonist as detailed herein. A control may be a subject, or a sample therefrom, whose disease state is known. The subject, or sample therefrom, may be healthy, diseased, diseased prior to treatment, diseased during treatment, or diseased after treatment, or a combination thereof.

As used herein, a disease or disorder of the central nervous system (CNS) refers to a disorder affecting either the spinal cord (e.g., a myelopathy) or brain (e.g., an encephalopathy) of a subject, which may present with neurological and/or psychiatric symptoms. CNS disorders include many various neurodegenerative diseases and psychiatric disorders. In some embodiments, the disease or disorder is a developmental disorder, a cognitive disorder, a degenerative disorder, a neuropsychiatric disorder, or brain injury. In some embodiments, the developmental disorder is Lissecephaly. In some embodiments, the cognitive disorder is selected from Angelman Syndrome and schizophrenia. In some embodiments, the degenerative disorder is Alzheimers disease. In some embodiments, the neuropsychiatric disorder is selected from schizophrenia and bipolar disorder In some embodiments, the brain injury is traumatic brain injury (TBI). In some embodiments, the disease or disorder is selected from Lissecephaly, fragile X syndrome, William's syndrome, Rett syndrome, Down's syndrome, Angelman syndrome, autism, ischemia, hypoxia, Alzheimers disease, Reelin deficiency, schizophrenia, bipolar disorder, neurodegeneration, traumatic brain injury, mental retardation, dementia, bipolar disorder, stroke, and age-related cognitive decline.

"Polynucleotide" as used herein can be single stranded or double stranded, or can contain portions of both double stranded and single stranded sequence. The polynucleotide can be nucleic acid, natural or synthetic, DNA, genomic DNA, cDNA, RNA, or a hybrid, where the polynucleotide can contain combinations of deoxyribo- and ribo-nucleotides, and combinations of bases including uracil, adenine, thymine, cytosine, guanine, inosine, xanthine hypoxanthine, isocytosine, and isoguanine. Polynucleotides can be obtained by chemical synthesis methods or by recombinant methods.

A "peptide" or "polypeptide" is a linked sequence of two or more amino acids linked by peptide bonds. The polypeptide can be natural, synthetic, or a modification or combination of natural and synthetic. Peptides and polypeptides include proteins such as binding proteins, receptors, and antibodies. The terms "polypeptide," "protein," and "peptide" are used interchangeably herein. "Primary structure" refers to the amino acid sequence of a particular peptide "Secondary structure" refers to locally ordered, three dimensional structures within a polypeptide. These structures are commonly known as domains, e.g., enzymatic domains, extracellular domains, transmembrane domains, pore domains, and cytoplasmic tail domains. "Domains" are portions of a polypeptide that form a compact unit of the polypeptide and are typically 15 to 350 amino acids long. Exemplary domains include domains with enzymatic activity or ligand binding activity. Typical domains are made up of sections of lesser organization such as stretches of beta-sheet and alpha-helices. "Tertiary structure" refers to the complete three dimensional structure of a polypeptide monomer. "Quaternary structure" refers to the three dimensional structure formed by the noncovalent association of independent tertiary units. A "motif" is a portion of a polypeptide sequence and includes at least two amino acids. A motif may be 2 to 20, 2 to 15, or 2 to 10 amino acids in length In some embodiments, a motif includes 3, 4, 5, 6, or 7 sequential amino acids. A domain may be comprised of a series of the same type of motif.

"Sample" or "test sample" as used herein can mean any sample in which the presence and/or level of a target is to be detected or determined or any sample comprising an agonist or lipoprotein receptor as detailed herein. Samples may include liquids, solutions, emulsions, or suspensions. Samples may include a medical sample. Samples may include any biological fluid or tissue, such as blood, whole blood, fractions of blood such as plasma and serum, muscle, interstitial fluid, sweat, saliva, urine, tears, synovial fluid, bone marrow, cerebrospinal fluid, nasal secretions, sputum, amniotic fluid, bronchoalveolar lavage fluid, gastric lavage, emesis, fecal matter, lung tissue, peripheral blood mononuclear cells, total white blood cells, lymph node cells, spleen cells, tonsil cells, cancer cells, tumor cells, bile, digestive fluid, skin, or combinations thereof. In some embodiments, the sample comprises an aliquot. In other embodiments, the sample comprises a biological fluid. Samples can be obtained by any means known in the art. The sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art.

"Subject" as used herein can mean a mammal that wants or is in need of the herein described agonists or methods. The subject may be a patient. The subject may be a human or a non-human animal. The subject may be a mammal. The mammal may be a primate or a non-primate. The mammal can be a primate such as a human; a non-primate such as, for example, dog, cat, horse, cow, pig, mouse, rat, camel, llama, goat, rabbit, sheep, hamster, and guinea pig; or non-human primate such as, for example, monkey, chimpanzee, gorilla, orangutan, and gibbon. The subject may be of any age or stage of development, such as, for example, an adult, an adolescent, or an infant. In some embodiments, the subject has a specific genetic marker.

"Substantially Identical" can mean that a first and second amino acid sequence are at least 60%, 65%, 70%, 75%, 80%, 85%, 90%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 amino acids.

"Treatment" or "treating," when referring to protection of a subject from a disease, means preventing, suppressing, repressing, ameliorating, or completely eliminating the disease. Preventing the disease involves administering a composition of the present invention to a subject prior to onset of the disease. Suppressing the disease involves administering a composition of the present invention to a subject after induction of the disease but before its clinical appearance. Repressing or ameliorating the disease involves administering a composition of the present invention to a subject after clinical appearance of the disease.

"Variant" as used herein with respect to a polynucleotide means (i) a portion or fragment of a referenced nucleotide sequence; (ii) the complement of a referenced nucleotide sequence or portion thereof; (iii) a polynucleotide that is substantially identical to a referenced polynucleotide or the complement thereof; or (iv) a polynucleotide that hybridizes under stringent conditions to the referenced polynucleotide, complement thereof, or a sequences substantially identical thereto.

A "variant" can further be defined as a peptide or polypeptide that differs in amino acid sequence by the insertion, deletion, or conservative substitution of amino acids, but retain at least one biological activity. Representative examples of "biological activity" include the ability to be bound by a specific antibody or polypeptide or to promote an immune response. Variant can mean a substantially identical sequence. Variant can mean a functional fragment thereof. Variant can also mean multiple copies of a polypeptide. The multiple copies can be in tandem or separated by a linker. Variant can also mean a polypeptide with an amino acid sequence that is substantially identical to a referenced polypeptide with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids. See Kyle at al., *J. Mol. Biol.* 1982, 157, 105-132. The hydropathic index of an amino acid is based on a consideration of its hydrophobicity and charge. It is known in the art that amino acids of similar hydropathic indexes can be substituted and still retain protein function. In one aspect, amino acids having hydropathic indices of ±2 are substituted. The hydrophobicity of amino acids can also be used to reveal substitutions that would result in polypeptides retaining biological function. A consideration of the hydrophilicity of amino acids in the context of a polypeptide permits calculation of the greatest local average hydrophilicity of that polypeptide, a useful measure that has been reported to correlate well with antigenicity and immunogenicity, as discussed in U.S. Pat. No. 4,554,101, which is fully incorporated herein by reference. Substitution of amino acids having similar hydrophilicity values can result in polypeptides retaining biological activity, for example immunogenicity, as is understood in the art. Substitutions can be performed with amino acids having hydrophilcity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties A variant can be a polynucleotide sequence that is substantially identical over the full length of the full gene sequence or a fragment thereof. The polynucleotide sequence can be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant can be an amino acid sequence that is substantially identical over the full length of the amino acid sequence or fragment thereof. The amino acid sequence can be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

2. REELIN

Reelin is a secreted extracellular matrix glycoprotein that helps regulate processes of neuronal migration and positioning in the developing brain by controlling cell, cell interactions. Reelin may modulate synaptic plasticity by enhancing the induction and maintenance of long-term potentiation, stimulate dendrite and dendritic spine development, and regulate the migration of neuroblasts generated in adult neurogenesis. Reelin may be found in, for example, the brain, spinal cord, blood, and other organs and tissues.

Full-length Reelin is a 450 kDa polypeptide. Full-length Reelin may be cleaved at two sites located after domains 2 and 6—approximately between repeats 2 and 3 and between repeats 6 and 7—resulting in the production of five smaller polypeptide fragments, including a 180 kDa polypeptide fragment.

3. LIPOPROTEIN RECEPTOR

Reelin may bind to a low density lipoprotein receptor. Low density lipoprotein receptors include, for example, VLDLR and apolipoprotein E receptor 2 (ApoER2). In some embodiments, the lipoprotein receptor comprises ApoER2. In some embodiments, the lipoprotein receptor comprises VLDLR. The lipoprotein receptors may influence brain development and function. VLDLR may conduct a stop signal, while ApoER2 has a role in the migration of late-born neocortical neurons. Both VLDLR and ApoER2 have in an internalization domain called the NPxY motif. After binding to the VLDLR or ApoER2 receptor. Reelin is internalized into the cell by endocytosis.

The interaction of Reelin with the lipoprotein receptor activates intracellular processes. The transmission of Reelin signals through the VLDLR and/or ApoER2 lipoprotein receptors may begin with the phosphorylation of DAB1. DAB1 may bind to the intracellular portion of the VLDLR or ApoER2 receptor. DAB1 may be phosphorylated by two tyrosine kinases, Fyn and Src. The phosphorylated DAB1 may then cause further activation of these two kinases and others, including a phosphatidylinositol-3-kinase (PI3K).

4. AGONISTS

Further provided herein are agonists of a lipoprotein receptor. The agonist may activate a Reelin signaling pathway. The agonist may activate a lipoprotein receptor independently of Reelin. In some embodiments, the agonist may dimerize or cluster the lipoprotein receptor. Activity of the agonist may be determined by measuring or monitoring an activity or level of a polypeptide in the Reelin signaling pathway. For example, the activity of an agonist may be determined by measuring the level of phosphorylation of DAB1. The activity of an agonist may be determined by measuring the expression of ApoER2. The activity of an agonist may be determined by measuring the dimerization of the VLDLR lipoprotein receptor, the dimerization of the ApoER2 lipoprotein receptor, or a combination thereof. The receptor may include a luciferase, fluorescent polypeptide, or other label to measure and monitor the dimerization. The activity of an agonist may be determined by measuring or monitoring an activity or level of downstream signaling linked to DAB-1 phosphorylation, including, for example, phosphorylation of extracellular regulated kinase (ERK), phosphoinositide 3-kinase (PI3K). Src family of Tyrosine kinases, or a combination thereof a. Compounds The agonist may be a compound according to Formula I'

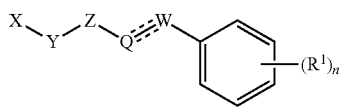

or a pharmaceutically acceptable salt thereof, wherein $R^1$ is independently hydrogen, halogen, hydroxyl, alkoxyl, or alkyl;

n is an integer from 0 to 5.

W is C, CH, $CH_2$, or O;

Q is C, CH, $CH_2$, N, or NH;

Z is C=O, NH, or $CH_2$;

Y is C=O, NH, or $CH_2$, or Z and Y may together form a bicyclic ring; and

X is cycloalkyl, cycloalkenyl, cycloakynyl, heterocyclyl, aryl, or heteroaryl, and may be unsubstituted or substituted with $(R^2)_m$, wherein $R^2$ is independently hydrogen, halogen, hydroxyl, alkoxyl, or alkyl, and m is an integer from 0 to 5.

In some embodiments of Formula I', $R^1$ is methoxy. In some embodiments of Formula I', $R^1$ is OH. In some embodiments of Formula I', $R^1$ is isopropyl. In some embodiments of Formula I', n is 1 or 2.

In some embodiments of Formula I', W is O, In some embodiments of Formula I', W is CH.

In some embodiments of Formula I', Q is N. In some embodiments of Formula I', Q is CH. In some embodiments of Formula I', Q is $CH_2$.

In some embodiments of Formula I', Z is NH. In some embodiments of Formula I', Z is C=O.

In some embodiments of Formula I', Y is NH In some embodiments of Formula I', Y is C=O.

In some embodiments of Formula I', Z and Y together form a bicyclic ring. In some embodiments of Formula I', Z and Y together form a heterobicyclic ring. In some embodiments of Formula I', Z and Y together form a heteroaryl ring. In some embodiments of Formula I', Z and Y together form benzimidazole.

In some embodiments of Formula I', X is aryl substituted with $(R^2)_m$. In some embodiments of Formula I', X is phenyl substituted with $(R^2)_m$.

In some embodiments of Formula I', $R^2$ is methyl. In some embodiments of Formula I', $R^2$ is Cl, I, F, or Br. In some embodiments of Formula I', $R^2$ is Cl or I.

In some embodiments of Formula r, m is 1 or 2.

In some embodiments, the agonist is a compound of Formula I', wherein $R^1$ is isopropyl, n is 1, W is CH, Q is CH, Z is C=O, Y is NH, and X is phenyl substituted with $(R^2)_m$, wherein $R^2$ is Cl and m is 1.

In some embodiments, the agonist is a compound of Formula I', wherein $R^1$ is isopropyl, n is 1, W is CH, Q is CH, Z is C=O, Y is NH and X is phenyl substituted with $(R^2)_m$, wherein $R^2$ is Cl and m is 2.

In some embodiments, the agonist is a compound of Formula I', wherein $R^1$ is isopropyl, n is 1, W is CH, Q is CH, Z is C=O, Y is NH, and X is phenyl substituted with $(R^2)_m$, wherein $R^2$ is Cl and m is 2.

In some embodiments, the agonist is a compound of Formula I', wherein $R^1$ is isopropyl, n is 1, W is CH, Q is CH, Z is C=O, Y is NH, and X is phenyl substituted with $(R^2)_m$, wherein $R^2$ is Cl and m is 1.

In some embodiments, the agonist is a compound of Formula I', wherein $R^1$ is isopropyl, n is 1, W is CH, Q is CH, Z is C=O, Y is NH, and X is phenyl substituted with $(R^2)_m$, wherein $R^2$ is independently Cl or I and m is 2.

In some embodiments, the agonist is a compound of Formula I', wherein $R^1$ is isopropyl, n is 1, W is CH, Q is CH, Z is C=O, Y is NH, and X is phenyl substituted with $(R^2)_m$, wherein $R^2$ is Cl and m is 1.

In some embodiments, the agonist is a compound of Formula I', wherein $R^1$ is independently OH and methoxy, n is 2, W is CH, Q is N, Z and Y together form benzimidazole, and X is phenyl substituted with $(R^2)_m$, wherein $R^2$ is Cl and m is 2.

In some embodiments, the agonist is a compound of Formula I', wherein $R^1$ is OH, n is 2, W is CH, Q is N, Z is NH, Y is C=O, and X is phenyl substituted with $(R^2)_m$, wherein $R^2$ is methyl and m is 1.

In some embodiments, the agonist is a compound of Formula I', wherein $R^1$ is Cl, n is 2, W is O, Q is $CH_2$, Z is C=O, Y is NH, and X is phenyl substituted with $(R^2)_m$, wherein $R^2$ is Cl and m is 1.

In some embodiments, compounds of Formula I' have a structure of Formula I.

The agonist may be a compound according to Formula I:

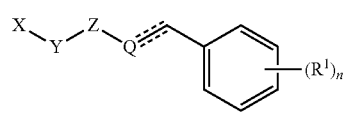

or a pharmaceutically acceptable salt thereof, wherein $R^1$ is independently hydrogen, halogen, hydroxyl, alkoxyl, or alkyl, n is an integer from 0 to 5;

Q is C, CH, $CH_2$, N, or NH;

Z is C=O, NH, or $CH_2$;

Y is C=O, NH, or $CH_2$, or Z and Y may together form a bicyclic ring; and

X is cycloalkyl, cycloalkenyl, cycloakynyl, heterocyclyl, aryl, or heteroaryl, and may be unsubstituted or substituted with $(R^2)_m$, wherein $R^2$ is independently hydrogen, halogen, hydroxyl, alkoxyl, or alkyl, and m is an integer from 0 to 5.

In some embodiments of Formula I, $R^1$ is methoxy. In some embodiments of Formula I, $R^1$ is OH. In some embodiments of Formula I, $R^1$ is isopropyl. In some embodiments of Formula I, n is 1 or 2.

In some embodiments of Formula I, Q is N. In some embodiments of Formula I, Q is CH.

In some embodiments of Formula I, Z is NH. In some embodiments of Formula I, Z is C=O.

In some embodiments of Formula I, Y is NH. In some embodiments of Formula I, Y is C=O.

In some embodiments of Formula I, Z and Y together form a bicyclic ring. In some embodiments of Formula I, Z and Y together form a heterobicyclic ring. In some embodiments of Formula I, Z and Y together form a heteroaryl ring. In some embodiments of Formula I, Z and Y together form benzimidazole.

In some embodiments of Formula I, X is aryl substituted with $(R^2)_m$. In some embodiments of Formula I, X is phenyl substituted with $(R^2)_m$.

In some embodiments of Formula I, $R^2$ is methyl. In some embodiments of Formula I, $R^2$ is Cl, I, F, or Br. In some embodiment of Formula I, $R^2$ is Cl or I.

In some embodiments of Formula I, m is 1 or 2.

In some embodiments, the agonist is a compound of Formula I, wherein $R^1$ is isopropyl, n is 1, Q is CH, Z is C=O, Y is NH, and X is phenyl substituted with $(R^2)_m$, wherein $R^2$ is Cl and m is 1.

In some embodiments, the agonist is a compound of Formula I, wherein $R^1$ is isopropyl, n is 1, Q is CH, Z is C=O, Y is NH, and X is phenyl substituted with $(R^2)_m$, wherein $R^2$ is Cl and m is 2.

In some embodiments, the agonist is a compound of Formula I, wherein $R^1$ is isopropyl, n is 1, Q is CH, Z is C=O, Y is NH, and X is phenyl substituted with $(R^2)_m$, wherein $R^2$ is Cl and m is 2.

In some embodiments, the agonist is a compound of Formula I, wherein $R^1$ is isopropyl, n is 1, Q is CH, Z is C=O, Y is NH, and X is phenyl substituted with $(R^2)_m$, wherein $R^2$ is Cl and m is 1.

In some embodiments, the agonist is a compound of Formula I, wherein $R^1$ is isopropyl, n is 1, Q is CH, Z is C=O, Y is NH, and X is phenyl substituted with $(R^2)_m$, wherein $R^2$ is Cl and I and m is 2.

In some embodiments, the agonist is a compound of Formula I, wherein $R^1$ is isopropyl, n is 1, Q is CH, Z is C=O, Y is NH, and X is phenyl substituted with $(R^2)_m$, wherein $R^2$ is Cl and m is 1.

In some embodiments, the agonist is a compound of Formula I, wherein $R^1$ is independently OH and methoxy, n is 2, Q is N, Z and Y together form benzimidazole, and X is phenyl substituted with $(R^2)_m$, wherein $R^2$ is Cl and m is 2.

In some embodiments, the agonist is a compound of Formula I, wherein $R^1$ is OH, n is 2, Q is N, Z is NH, Y is C=O, and X is phenyl substituted with $(R^2)_m$, wherein $R^2$ is methyl and m is 1.

The agonist may be a compound according to Formula II:

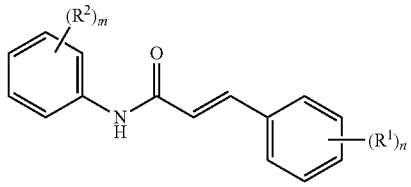

(II)

or a pharmaceutically acceptable salt thereof,
wherein $R^1$ is independently hydrogen, halogen, hydroxyl, alkoxyl, or alkyl;
n is an integer from 0 to 5;
$R^2$ is independently hydrogen, halogen, hydroxyl, alkoxyl, or alkyl; and
m is an integer from 0 to 5.

In some embodiments or Formula II, $R^1$ is $C_{1-4}$ alkyl. In some embodiments of Formula II, $R^1$ is methyl, ethyl, or isopropyl In some embodiments of Formula II, $R^2$ is Cl, I, F, or Br. In some embodiments of Formula II, $R^2$ is Cl or I. In some embodiments of Formula II, m is 1 or 2.

In some embodiments, the agonist is a compound of Formula II, wherein $R^2$ is Cl, m is 1, $R^1$ is isopropyl, and n is 1

In some embodiments, the agonist is a compound of Formula II, wherein $R^2$ is Cl, m is 2, $R^1$ is isopropyl, and n is 1.

In some embodiments, the agonist is a compound of Formula II, wherein $R^2$ is Cl, m is 2, $R^1$ is isopropyl, and n is 1

In some embodiments, the agonist is a compound of Formula II, wherein $R^2$ is Cl, m is 1, $R^1$ is isopropyl, and n is 1

In some embodiments, the agonist is a compound of Formula II, wherein $R^2$ is independently Cl or I, m is 2, $R^1$ is isopropyl, and n is 1.

In some embodiments, the agonist is a compound of Formula II, wherein $R^2$ is Cl, m is 1, $R^1$ is isopropyl, and n is 1.

In some embodiments of Formula II, $R^2$ is Cl, I, F, or Br, and m is 1. In some embodiments of Formula II, $R^2$ is Cl or I and m is 1.

The agonist may be a compound according to Formula III:

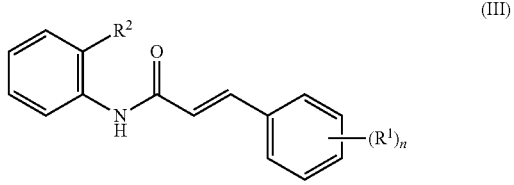

(III)

or a pharmaceutically acceptable salt thereof,
wherein each $R^1$ is independently hydrogen, halogen, hydroxyl, alkoxyl, or alkyl;
n is an integer from 0 to 5; and
$R^2$ is hydrogen, halogen, hydroxyl, alkoxyl, or alkyl In some embodiments of Formula III, $R^1$ is $C_{1-4}$ alkyl. In some embodiments of Formula III, $R^1$ is methyl, ethyl, or isopropyl. In some embodiments of Formula III, $R^1$ is isopropyl in some embodiments of Formula III, n is 1 or 2.

In some embodiments of Formula III, $R^2$ is Cl, I, F, or Br. In some embodiments of Formula III, $R^2$ is Cl or I. In some embodiments of Formula III, $R^2$ is Cl.

In some embodiments, the agonist is a compound of Formula III, wherein $R^2$ is Cl, $R^1$ is isopropyl, and n is 1.

In some embodiments, the agonist comprises one of the following compounds;

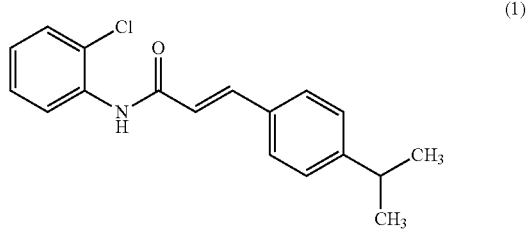

N-(2-chlorophenyl)-3-(4-isopropylphenyl)acrylamide
(Relact02)
$C_{18}H_{18}ClNO$ (1)

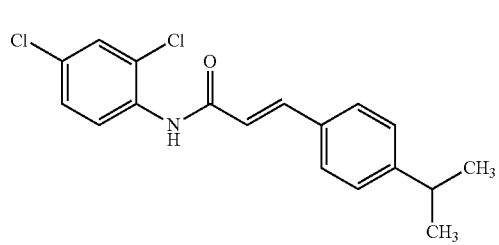

N-(2,4-dichlorophenyl)-3-(4-isopropylphenyl)acrylamide
$C_{18}H_{17}Cl_2NO$ (2)

(3)

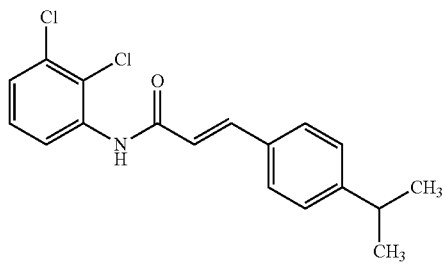

N-(2,3-dichlorophenyl)-3-(4-isopropylphenyl)acrylamide
$C_{18}H_{17}Cl_2NO$ (4)

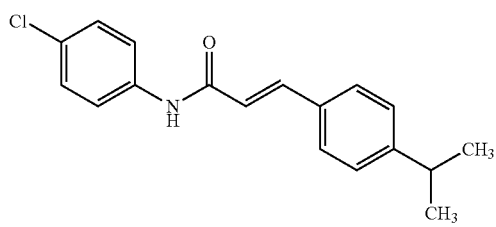

N-(4-chlorophenyl)-3-(4-isopropylphenyl)acrylamide
$C_{18}H_{18}ClNO$ (5)

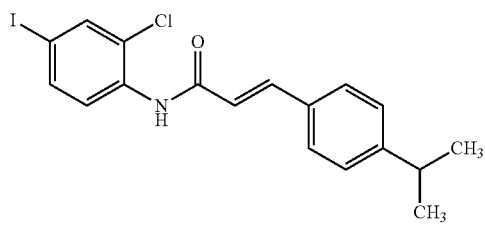

N-(2-chloro-4-iodophenyl)-3-(4-isopropylphenyl)acrylamide
$C_{18}H_{17}ClINO$ (6)

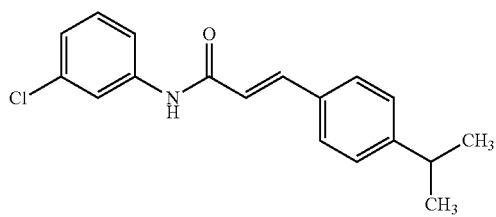

N-(3-chlorophenyl)-3-(4-isopropylphenyl)acrylamide
(Relact05)
$C_{18}H_{18}ClNO$ (7)

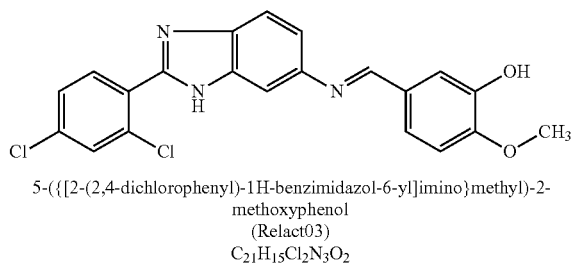

5-({[2-(2,4-dichlorophenyl)-1H-benzimidazol-6-yl]imino}methyl)-2-methoxyphenol
(Relact03)
$C_{21}H_{15}Cl_2N_3O_2$ (8)

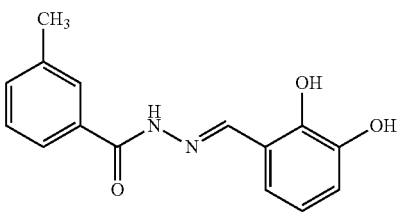

N'-(2,3-dihydroxybenzylidene)-3-methylbenzohydrazide
$C_{15}H_{14}N_2O_3$ (9)

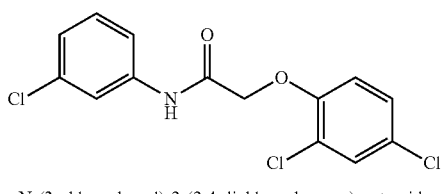

N-(3-chlorophenyl)-2-(2,4-dichlorophenoxy)acetamide
(Relact04)
$C_{14}H_{10}Cl_3NO_2$ or a pharmaceutically acceptable salt thereof.

In some embodiments, the agonist does not comprise at least one of the following compounds:

(2)

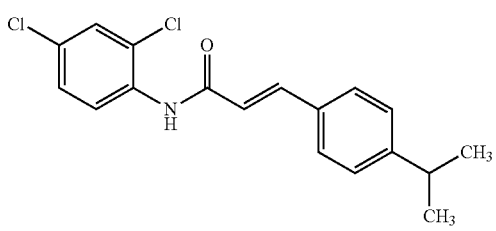

N-(2,4-dichlorophenyl)-3-(4-isopropylphenyl)acrylamide
$C_{18}H_{17}Cl_2NO$ (3)

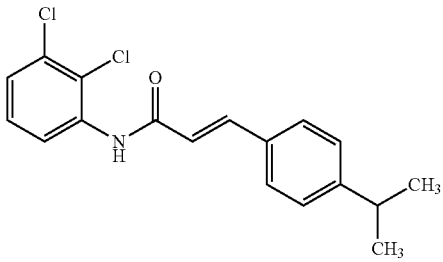

N-(2,3-dichlorophenyl)-3-(4-isopropylphenyl)acrylamide
$C_{18}H_{17}Cl_2NO$ (4)

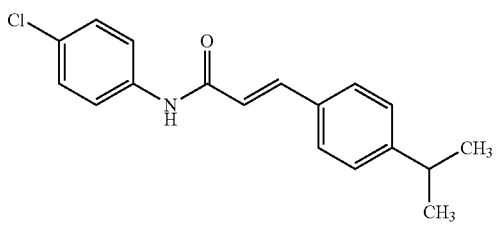

N-(4-chlorophenyl)-3-(4-isopropylphenyl)acrylamide
$C_{18}H_{18}ClNO$

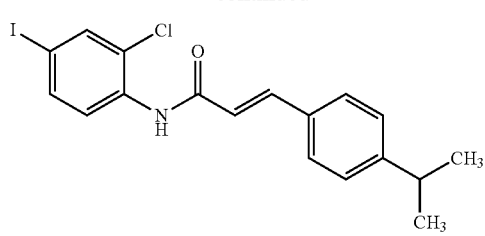

N-(2-chloro-4-iodophenyl)-3-(4-isopropylphenyl)acrylamide
$C_{18}H_{17}ClINO$ (5)

or a pharmaceutically acceptable salt thereof.

The compound may exist as a stereoisomer wherein asymmetric or chiral centers are present. The stereoisomer is "R" or "S" depending on the configuration of substituents around the chiral carbon atom. The terms "R" and "S" used herein are configurations as defined in IUPAC 1974 Recommendations for Section E. Fundamental Stereochemistry, in *Pure Appl. Chem.,* 1976, 45, 13-30. The disclosure contemplates various stereoisomers and mixtures thereof and these are specifically included within the scope of this invention. Stereoisomers include enantiomers and diastereomers, and mixtures of enantiomers or diastereomers. Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry." 5th edition (1989), Longman Scientific & Technical, Essex CM20 2JE. England, or (2) direct separation of the mixture of optical enantiomers on chiral chromatographic columns, or (3) fractional recrystallization methods.

It should be understood that the compound may possess tautomeric forms, as well as geometric isomers, and that these also constitute embodiments of the disclosure.

The present disclosure also includes an isotopically-labeled compound, which is identical to those recited in Formulas I' and I and II and III, but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Substitution with heavier isotopes such as deuterium, i.e. $^{2}H$, can afford certain therapeutic advantages resulting from greater metabolic stability, for example increased n vivo half-life or reduced dosage requirements and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in compounds of Formulas I' and I and II and III are $^{11}C$, $^{13}N$, $^{15}O$, and $^{18}F$. Isotopically-labeled compounds of Formulas I' and I and II and III can generally be prepared by conventional techniques known to those skilled in the art or by processes analogous to those described in the accompanying Examples using appropriate isotopically-labeled reagent in place of non-isotopically-labeled reagent.

b. Pharmaceutically Acceptable Salts

The disclosed compounds may exist as pharmaceutically acceptable salts. The term "pharmaceutically acceptable salt" refers to salts or zwitterions of the compounds which are water or oil-soluble or dispersible, suitable for treatment of disorders without undue toxicity, irritation, and allergic response, commensurate with a reasonable benefit/risk ratio and effective for their intended use. The salts may be prepared during the final isolation and purification of the compounds or separately by reacting an amino group of the compounds with a suitable acid. For example, a compound may be dissolved in a suitable solvent, such as but not limited to methanol and water and treated with at least one equivalent of an acid, like hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthalenesulfonate, nicotinate, oxalate, pamoate, pectinate, persulfate, 3-phenylpropionate, picrate, oxalate, maleate, pivalate, propionate, succinate, tartrate, trichloroacetate, trifluoroacetate, glutamate, para-toluenesulfonate, undecanoate, hydrochloric, hydrobromic, sulfuric, phosphoric, and the like. The amino groups of the compounds may also be quaternized with alkyl chlorides, bromides and iodides such as methyl, ethyl, propyl, isopropyl, butyl, lauryl, myristyl, stearyl, and the like.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

c. Synthesis of Compounds

Compounds as detailed herein are commercially available, for example, from Chembridge Corporation (San Diego, Calif.). Alternatively, the compounds as detailed herein may be synthetically made by methods known to one of skill in the art.

d. Pharmaceutical Compositions

The compounds as detailed herein may be formulated into pharmaceutical compositions in accordance with standard techniques well known to those skilled in the pharmaceutical art. The composition may comprise the compound and a pharmaceutically acceptable carrier. The term "pharmaceutically acceptable carrier," as used herein, means a non-toxic, inert solid, semi-solid or liquid filler, diluent, encapsulating material or formulation auxiliary of any type.

The route by which the disclosed compounds are administered and the form of the composition will dictate the type of carrier to be used. The pharmaceutical composition may be in a variety of forms, suitable, for example, for systemic administration (e.g., oral, rectal, sublingual, buccal, implants, intranasal, intravaginal, transdermal, intravenous, intraarterial, intratumoral, intraperitoneal, or parenteral) or topical administration (e.g., dermal, pulmonary, nasal, aural, ocular, liposome delivery systems, or iontophoresis). In some embodiments, the pharmaceutical composition is for administration to a subject's central nervous system. Techniques and formulations may generally be found in "Remington's Pharmaceutical Sciences." (Meade Publishing Co., Easton. Pa.). Pharmaceutical compositions must typically be sterile and stable under the conditions of manufacture and storage. All carriers are optional in the compositions.

Pharmaceutically acceptable carriers include, for example, diluents, lubricants, binders, disintegrants, colorants, flavors, sweeteners, antioxidants, preservatives, glidants, solvents, suspending agents, wetting agents, surfactants, emollients, propellants, humectants, powders, pH adjusting agents, and combinations thereof.

Suitable diluents include, for example, sugars such as glucose, lactose, dextrose, and sucrose; diols such as propylene glycol; calcium carbonate; sodium carbonate; sugar alcohols, such as glycerin; mannitol; sorbitol; cellulose; starch; and gelatin. The amount of diluent(s) in a systemic or topical composition may typically be about 50 to about 90%.

Suitable lubricants include, for example, silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil, and oil of theobroma. The amount of lubricant(s) in a systemic or topical composition may typically be about 5 to about 10%.

Suitable binders include, for example, polyvinyl pyrrolidone, magnesium aluminum silicate; starches such as corn starch and potato starch; gelatin; tragacanth; sucrose; and cellulose and its derivatives, such as sodium carboxymethylcellulose, ethyl cellulose, methylcellulose, microcrystalline cellulose, and hydroxypropyl methylcellulose. The amount of binder(s) in a systemic composition may typically be about 5 to about 50%.

Suitable disintegrants include, for example, agar, alginic acid and the sodium salt thereof, effervescent mixtures, croscarmellose, crospovidone, sodium carboxymethyl starch sodium starch glycolate, clays, and ion exchange resins. The amount of disintegrant(s) in a systemic or topical composition may typically be about 0.1 to about 10%.

Suitable colorants include, for example, a colorant such as an FD&C dye. When used, the amount of colorant in a systemic or topical composition may typically be about 0.005 to about 0.1%.

Suitable flavors include, for example, menthol, peppermint, and fruit flavors. The amount of flavor(s), when used, in a systemic or topical composition may typically be about 0.1 to about 1.0%.

Suitable sweeteners include, for example, aspartame and saccharin, or a combination thereof. The amount of sweetener(s) in a systemic or topical composition may typically be about 0.001 to about 1%.

Suitable antioxidants include, for example, butylated hydroxyanisole ("BHA"), butylated hydroxytoluene ("BHT"), and vitamin E. The amount of antioxidant(s) in a systemic or topical composition may typically be about 01 to about 5%.

Suitable preservatives include, for example, benzalkonium chloride, methyl paraben, and sodium benzoate. The amount of preservative(s) in a systemic or topical composition may typically be about 0.01 to about 5%.

Suitable glidants include, for example, silicon dioxide. The amount of glidant(s) in a systemic or topical composition may typically be about 1 to about 5%.

Suitable solvents include, for example, water, isotonic saline, ethyl oleate, glycerine, castor oils, hydroxylated castor oils, alcohols such as ethanol or isopropanol, methylene chloride, ethylene glycol monoethyl ether, diethylene glycol monobutyl ether, diethylene glycol monoethyl ether, dimethylsulfoxide, dimethyl formamide, tetrahydrofuran, and phosphate buffer solutions, and combinations thereof. The amount of solvent(s) in a systemic or topical composition is typically from about 0 to about 100%, or 0% to about 95%.

Suitable suspending agents include, for example, AVICEL RC-591 (from FMC Corporation of Philadelphia, Pa.) and sodium alginate. The amount of suspending agent(s) in a systemic or topical composition may typically be about 1 to about 8%.

Suitable surfactants include, for example, lecithin. Polysorbate 80, and sodium lauryl sulfate, and the TWEENS from Atlas Powder Company of Wilmington, Del. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of surfactant(s) in the systemic or topical composition may typically be about 0.1% to about 5%.

Suitable emollients include, for example, stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane. The amount of emollient(s) in a skin-based topical composition may typically be about 5% to about 95%.

Suitable propellants include, for example, propane, butane, isobutane, dimethyl ether, carbon dioxide, nitrous oxide, and combinations thereof. The amount of propellant in a topical composition may be about 0% to about 95%.

Suitable humectants include, for example, glycerin, sorbitol, sodium 2-pyrrolidone-5-carboxylate, soluble collagen, dibutyl phthalate, gelatin, and combinations thereof. The amount of humectant in a topical composition may be about 0% to about 95%.

Suitable powders include, for example, beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified Montmorillonite clay, hydrated aluminum silicate, fumed silica, carboxyvinyl polymer, sodium carboxymethyl cellulose, ethylene glycol monostearate, and combinations thereof. The amount of powder(s) in a topical composition may typically be 0% to 95%.

Suitable pH adjusting additives include, for example, HCl or NaOH in amounts sufficient to adjust the pH of a topical pharmaceutical composition.

In some embodiments, the pharmaceutically acceptable carrier is a sugar such as lactose, glucose, and sucrose. In some embodiments, the pharmaceutically acceptable carrier is a starch such as, for example, corn starch and potato starch. In some embodiments, the pharmaceutically acceptable carrier is cellulose and its derivatives such as, but not limited to, sodium carboxymethyl cellulose, ethyl cellulose and cellulose acetate.

In some embodiments, the pharmaceutically acceptable carrier is powdered tragacanth, malt, gelatin, or talc. In some embodiments, the pharmaceutically acceptable carrier is an excipient such as, but not limited to, cocoa butter and suppository waxes. In some embodiments, the pharmaceutically acceptable carrier is oil such as, but not limited to, peanut oil, cottonseed oil, safflower oil, sesame oil, olive oil, corn oil and soybean oil. In some embodiments, the pharmaceutically acceptable carrier is a glycol, such as propylene glycol. In some embodiments, the pharmaceutically acceptable carrier is an ester such as, but not limited to, ethyl oleate and ethyl laurate. In some embodiments, the pharmaceutically acceptable carrier is an agar. In some embodiments, the pharmaceutically acceptable carrier is a buffering agent such as, but not limited to, magnesium hydroxide and aluminum hydroxide. In some embodiments, the pharmaceutically acceptable carrier is alginic acid, pyrogen-free water, isotonic saline, Ringer's solution, ethyl alcohol, or a phosphate buffer solution. In some embodiments, the pharmaceutically acceptable carrier is a non-toxic compatible lubricant such as, but not limited to, sodium lauryl sulfate and magnesium stearate.

Compositions for oral administration can have various dosage forms. For example, solid forms include tablets, capsules, granules, and bulk powders. Tablets can be compressed, tablet triturates, enteric-coated, sugar-coated, film-coated, or multiple-compressed. Tablets typically include an active component, and a carrier comprising ingredients selected from diluents, lubricants, binders, disintegrants, colorants, flavors, sweeteners, glidants, and combinations thereof. Capsules (including implants, time release, and sustained release formulations) typically include a compound (e.g., a compound of Formula I' or I or II or III), and a carrier including one or more diluents disclosed above in a capsule comprising gelatin. Granules typically comprise a compound, and preferably glidants such as silicon dioxide to improve flow characteristics. Implants can be of the biodegradable or the non-biodegradable type.

Compositions for oral administration can have solid forms. Solid oral compositions may be coated by conventional methods, typically with pH or time-dependent coatings, such that a disclosed compound is released in the gastrointestinal tract in the vicinity of the desired application, or at various points and times to extend the desired action. The coatings typically include one or more components selected from the group consisting of cellulose acetate phthalate, polyvinyl acetate phthalate, hydroxypropyl methyl cellulose phthalate, ethyl cellulose, EUDRAGIT® coatings (available from Evonik Industries of Essen, Germany), waxes, and shellac.

Compositions for oral administration can have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically include a compound and a carrier, namely, a carrier selected from diluents, colorants, flavors, sweeteners, preservatives, solvents, suspending agents, and surfactants. Peroral liquid compositions preferably include one or more ingredients selected from colorants, flavors, and sweeteners.

Compositions for topical administration can be applied locally to the skin and may be in any form including solids, solutions, oils, creams, ointments, gels, lotions, shampoos, leave-on and rinse-out hair conditioners, milks, cleansers, moisturizers, sprays, skin patches, and the like. The carrier of the topical composition preferably aids penetration of the compounds into the skin. In the topical compositions, the carrier includes a topical carrier. Suitable topical carriers can include one or more ingredients selected from phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propenoate, dimethyl isosorbide, castor oil, combinations thereof, and the like. More particularly, carriers for skin applications may include propylene glycol, dimethyl isosorbide, and water, and even more particularly, phosphate buffered saline, isotonic water, deionized water, monofunctional alcohols, and symmetrical alcohols. The carrier of a topical composition may further include one or more ingredients selected from emollients, propellants, solvents, humectants, thickeners, powders, fragrances, pigments, and preservatives, all of which are optional.

Although the amounts of components in the compositions may vary depending on the type of composition prepared, in general, systemic compositions may include 0.01% to 50% of a compound (e.g., a compound of Formula I' or I or II or III) and 50% to 99.99% of one or more carriers. Compositions for parenteral administration may typically include 0.1% to 10% of a compound and 90% to 99.9% of one or more carriers. Oral dosage forms may include, for example, at least about 5%, or about 25% to about 50% of a compound. The oral dosage compositions may include about 50% to about 95% of carriers, or from about 50% to about 75% of carriers. The amount of the carrier employed in conjunction with a disclosed compound is sufficient to provide a practical quantity of composition for administration per unit dose of the compound. Techniques and compositions for making dosage forms useful in the methods of this invention are described in the following references; Modern Pharmaceutics. Chapters 9 and 10, Banker & Rhodes, eds. (1979); Lieberman et al., Pharmaceutical Dosage Forms; Tablets (1981); and Ansel. Introduction to Pharmaceutical Dosage Forms, 2nd Ed., (1976).

e. Administration

The compounds as detailed herein, or the pharmaceutical compositions comprising the same, may be administered to a subject. Such compositions comprising a compound can be administered in dosages and by techniques well known to those skilled in the medical arts taking into consideration such factors as the age, sex, weight, and condition of the particular subject, and the route of administration.

The compound can be administered prophylactically or therapeutically. In prophylactic administration, the compound can be administered in an amount sufficient to induce a response. In therapeutic applications, the compounds are administered to a subject in need thereof in an amount sufficient to elicit a therapeutic effect. An amount adequate to accomplish this is defined as "therapeutically effective amount." Amounts effective for this use will depend on, e.g., the particular composition of the compound regimen administered, the manner of administration, the stage and severity of the disease, the general state of health of the patient, and the judgment of the prescribing physician. A therapeutically effective amount is also one in which any toxic or detrimental effects of a compound of the invention (e.g., a compound of Formula I' or I or II or III) are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

For example, a therapeutically effective amount of a compound of Formula I' or I or II or III, may be about 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

The compound can be administered by methods well known in the art as described in Donnelly et al. (*Ann. Rev. Immnol.* 1997, 15, 617-648); Feigner et al. (U.S. Pat. No. 5,580,859, issued Dec. 3, 1996); Feigner (U.S. Pat. No. 5,703,055, issued Dec. 30, 1997); and Carson et al (U.S. Pat. No. 5,679,647, issued Oct. 21, 1997), the contents of all of which are incorporated herein by reference in their entirety. The compound can be complexed to particles or beads that can be administered to an individual, for example, using a vaccine gun. One skilled in the art would know that the choice of a pharmaceutically acceptable carrier, including a physiologically acceptable compound, depends, for example, on the route of administration.

The compound can be delivered via a variety of routes. Typical delivery routes include parenteral administration, e.g., intradermal, intramuscular or subcutaneous delivery. Other routes include oral administration, intranasal, intravaginal, transdermal, intravenous, intraarterial, intratumoral, intraperitoneal, and epidermal routes. In some embodiments, the compound is administered intravenously, intraarterially, or intraperitoneally to the subject. In some embodiments, the compound is administered to the central nervous system of the subject. In some embodiments, the compound is administered to the subject orally.

5. METHODS a. Methods of Treating a Disease or Disorder

Provided herein are methods of treating a disease or disorder in a subject in need thereof. In some embodiments, the methods include administering to the subject an agonist of a lipoprotein receptor as detailed herein. In some embodiments, the disease or disorder is of the central nervous system. In some embodiments, the disease or disorder is a developmental disorder, a cognitive disorder, a degenerative disorder, a neuropsychiatric disorder, or brain injury. In some embodiments, the developmental disorder is Lissecephaly In some embodiments, the cognitive disorder is selected from Angelman Syndrome and schizophrenia. In some embodiments, the degenerative disorder is Alzheimers disease. In some embodiments, the neuropsychiatric disorder is selected from schizophrenia and bipolar disorder. In some embodiments, the brain injury is traumatic brain injury (TBI). In some embodiments, the disease or disorder is selected from Lissecephaly, fragile X syndrome, William's syndrome, Rett syndrome, Down's syndrome, Angelman syndrome, autism, ischemia, hypoxia, Alzheimers disease, Reelin deficiency, schizophrenia, bipolar disorder, neurodegeneration, traumatic brain injury, mental retardation, dementia, bipolar disorder, and stroke.

b. Methods of Improving Cognitive Function

Provided herein are methods of improving cognitive function in a subject in need thereof. In some embodiments, the methods include administering to the subject an agonist of a lipoprotein receptor as detailed herein.

c. Methods of Increasing Dendritic Spine Density

Provided herein are methods of increasing dendritic spine density in a subject in need thereof. In some embodiments, the methods include administering to the subject an agonist of a lipoprotein receptor as detailed herein.

d. Methods of Improving Associative Learning

Provided herein are methods of improving associative learning in a subject in need thereof. In some embodiments, the methods include administering to the subject an agonist of a lipoprotein receptor as detailed herein.

e. Methods of Improving Spatial Learning

Provided herein are methods of Improving spatial learning in a subject in need thereof. In some embodiments, the methods include administering to the subject an agonist of a lipoprotein receptor as detailed herein.

f. Methods of Improving Long-Term Potentiation of Neurons

Provided herein are methods of improving long-term potentiation of neurons in a subject in need thereof. In some embodiments, the methods include administering to the subject an agonist of a lipoprotein receptor as detailed herein.

g. Methods of Activating a Lipoprotein Receptor

Provided herein are methods of activating a lipoprotein receptor in a subject in need thereof. In some embodiments, the methods include administering to the subject an agonist of a lipoprotein receptor as detailed herein.

6. EXAMPLES

Example 1

Compound Screening with ApoER2 Luciferase Assay

Figure 3:
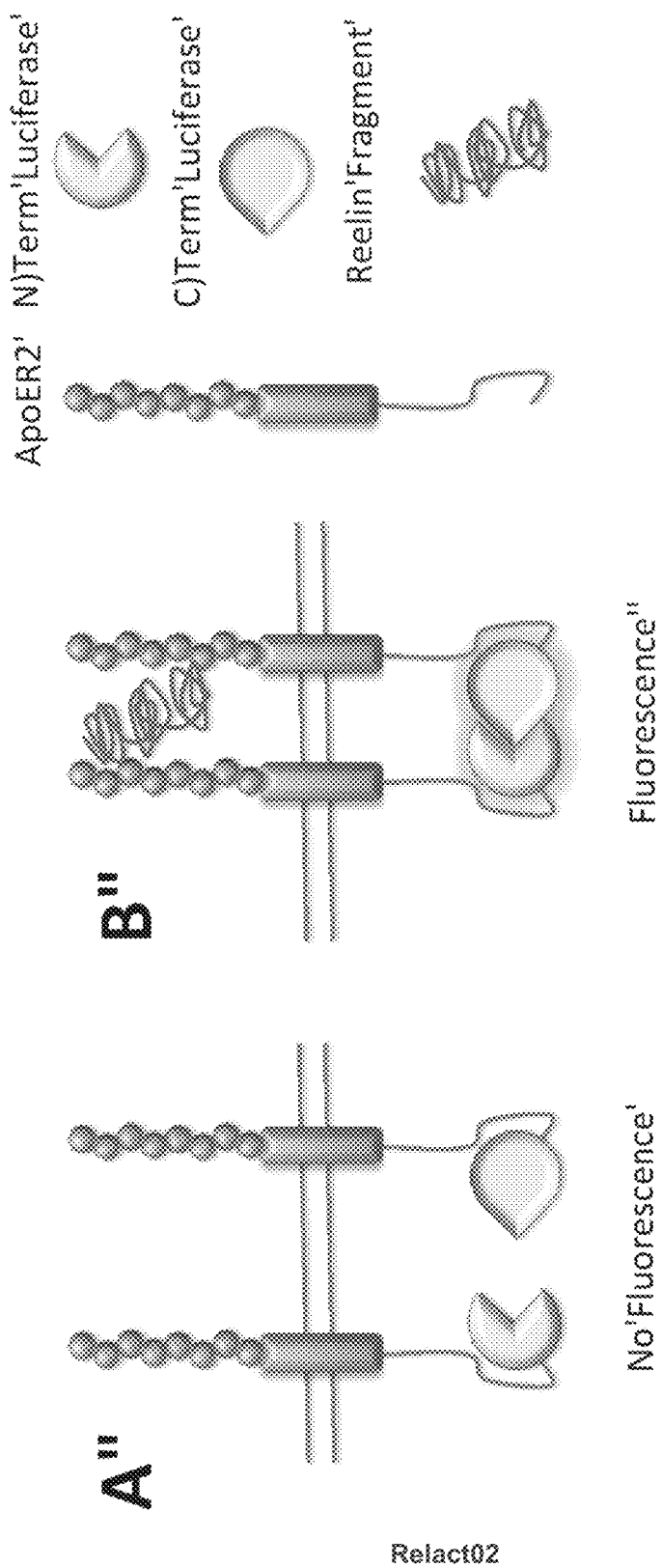
FIG. 3 is a schematic of the ApoER2 Clustering Assay. The ApoER2 clustering assay uses the co-transfection of ApoER2 fusion proteins that express either the C- or N-terminal of the luciferase enzyme (A") Upon Reelin fragment binding, receptor clustering results in active Luciferase and detectable fluorescence (B"). Controls included non-transfected Hek293 cells. Results are average +/−SEM; n=9-15 assays per fragment
Figure 4A:
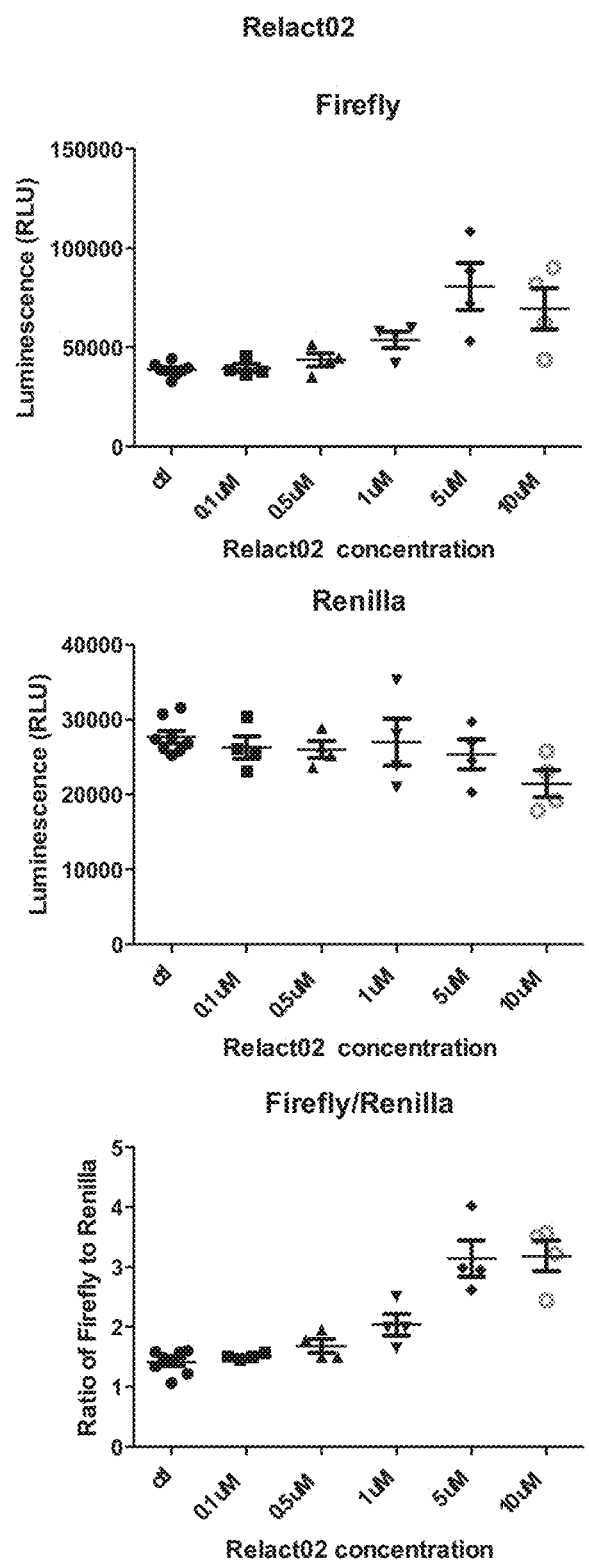
FIG. 4A, FIG. 4B, FIG. 4C, and FIG. 4D are graphs of luminescence versus compound concentration according to the ApoER2 luciferase assay for Relact02 (FIG. 4A), Relact03 (FIG. 4B), Relact04 (FIG. 4C), and Relact05 (FIG. 4D). Renilla is a constant florescence enzyme that controls for the quantification of viable cells in the 96-well plate. The ratio of firefly/renilla shows firefly florescence within a quantifiable number of cells in culture.
Figure 4B:
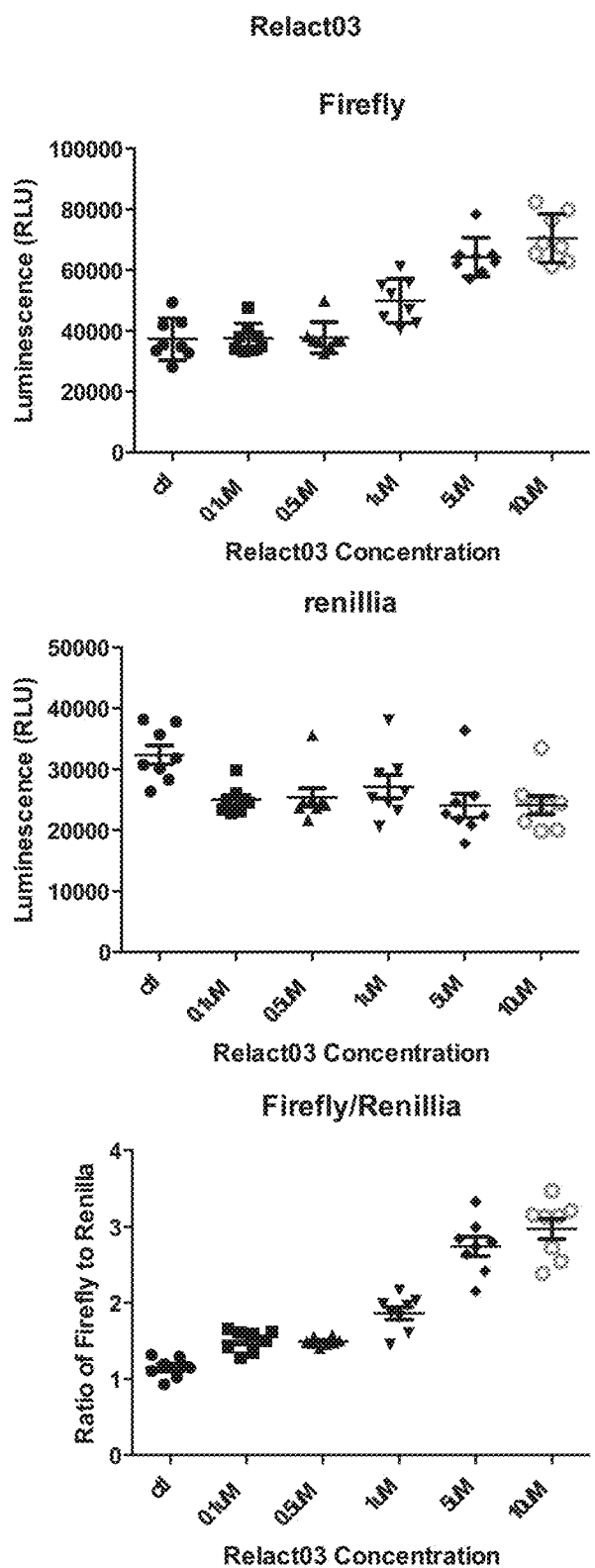
Figure 4C:
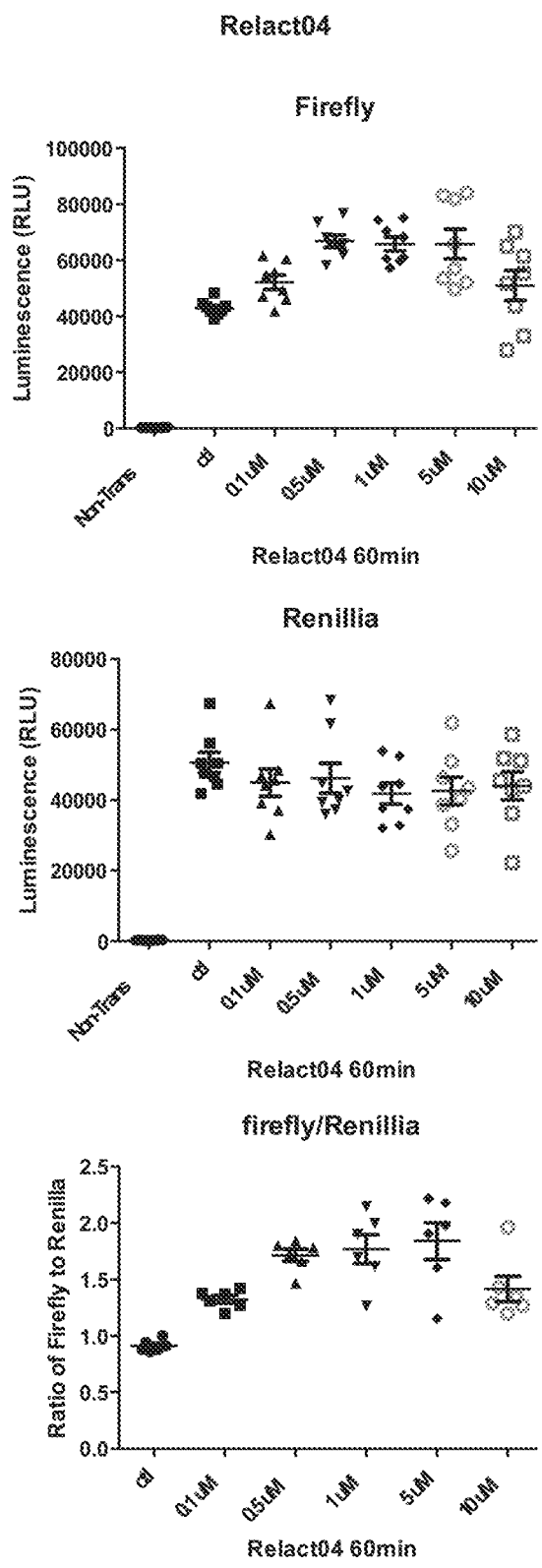
Figure 4D:
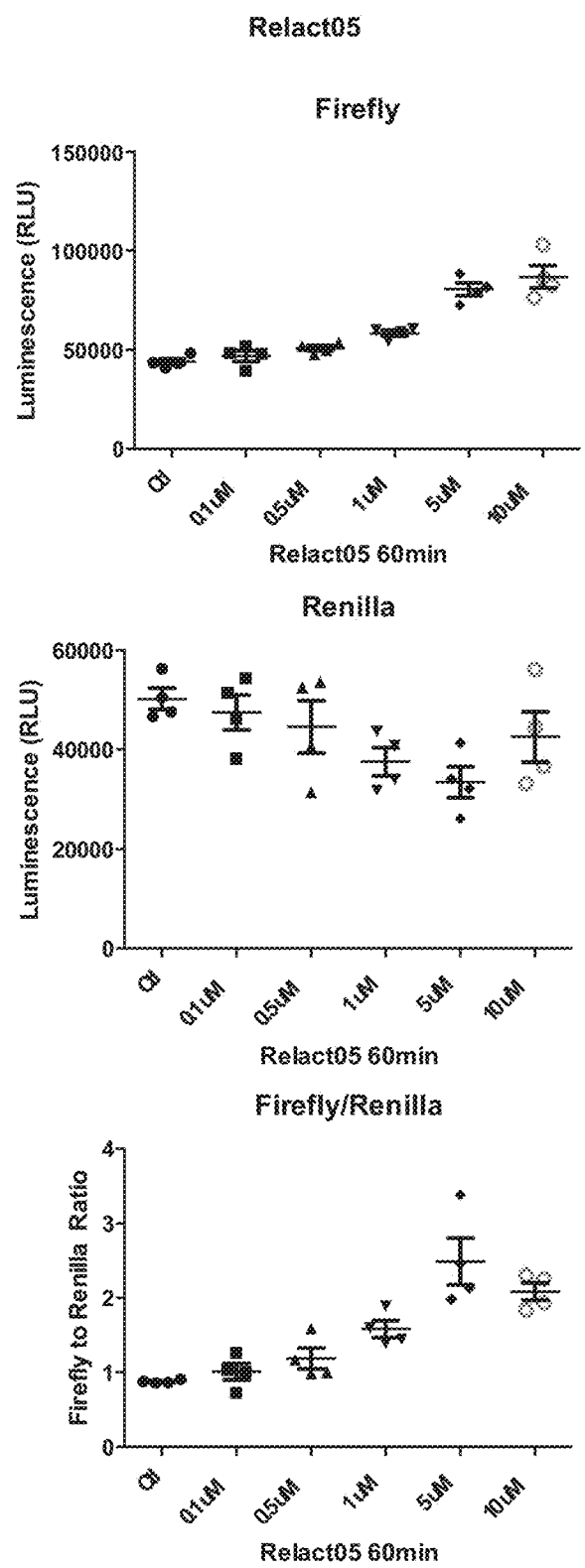

Reelin is able to signal through ApoER2 and VLDLR by clustering the receptors. Receptor clustering results in Dab1 activation and is responsible for the modulation of LTP in wild-type acute hippocampal slices. The ApoER2 luciferase assay was used to measure ApoER2 dimerization. This system used an ApoER2-luciferase fusion protein in which ApoER2 was coupled with either the N- or C-terminus portion of luciferase. Upon receptor clustering, the N- and C-terminus portions of luciferase combined to produce a quantifiable fluorescent signal. As a control, all cells were transfected with a Renilla florescent protein that quantified the number of cells in the testing well. The ratio of luciferase florescence to Renilla florescence was used to determine the effect of small molecules. The ApoER2 luciferase assay (FIG. 3) was used to identify small molecules that mimic the actions of Reelin to activate the Reelin signaling system.

The CNS-Set Library was purchased from ChemBridge® and consisted of 35,000 small molecule compounds. The effects of each compound on Reelin signaling were tested in the absence or presence of purified Reeling with the ApoER2 luciferase assay in a 96-well plate. The assay was used to identify agonists of ApoER2 clustering and luciferase activity and was not particularly sensitive for identifying antagonists of receptor clustering.

Approximately 2,700 compounds were tested and 4 unique compounds were identified having significant activation properties in the ApoER2 luciferase assay. Each of the 4 compounds had positive results in the absence of Reelin, suggesting each compound is a direct agonist for ApoER2 clustering and not an allosteric modulator of Reelin-Induced signaling. The 4 compounds were designated Relact02 (1), Relact03 (7), Relact04 (9), and Relact05 (6), as detailed above. In addition, a negative control compound (E02, ethyl 5-((benzylamino)carbonyl)-2-methyl-6-oxo-1,6-dihydro-3-pyridinecarboxylate) showed no luciferase activity.

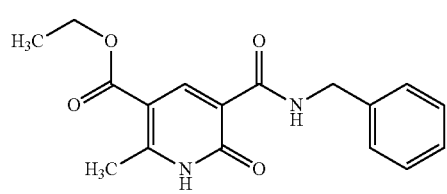

E02

Figure 5A:
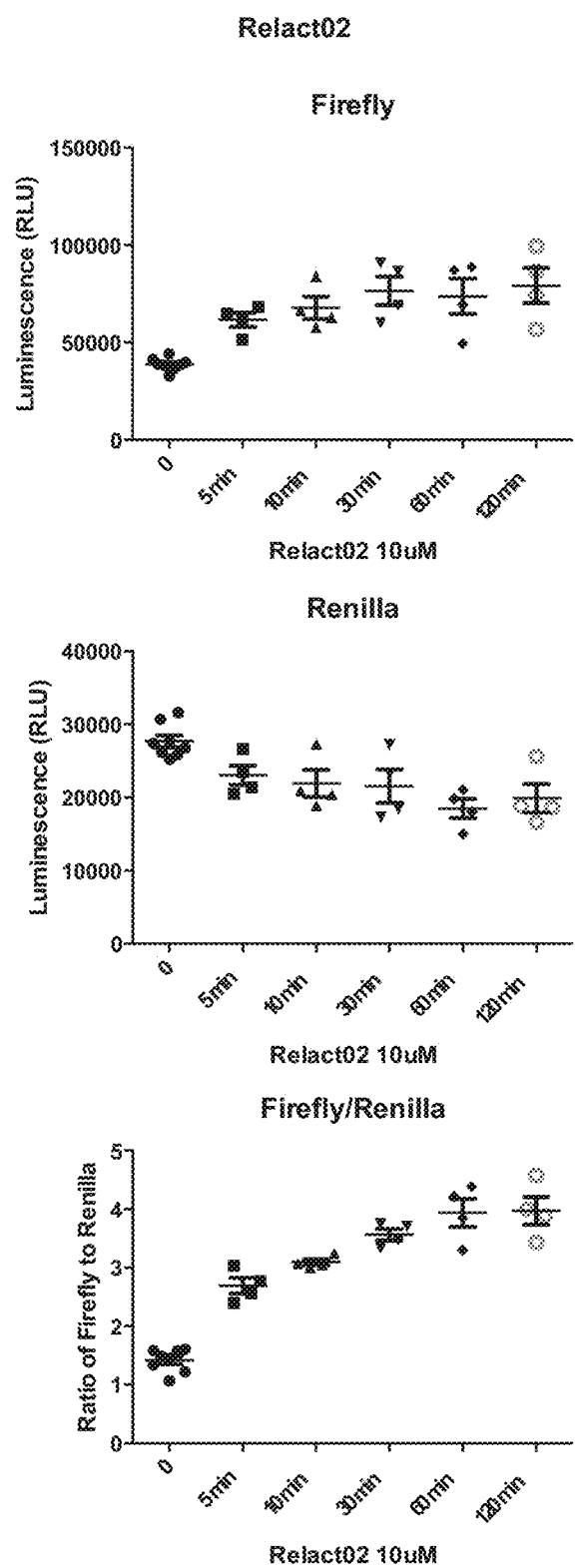
FIG. 5A and FIG. 5B are time course graphs for Relact02 (FIG. 5A) and Relact03 (FIG. 5B) in the ApoER2 luciferase assay using the optimum concentration as determined in the Dose Response Curves (FIG. 4A and FIG. 4B, respectively).
Figure 5B:
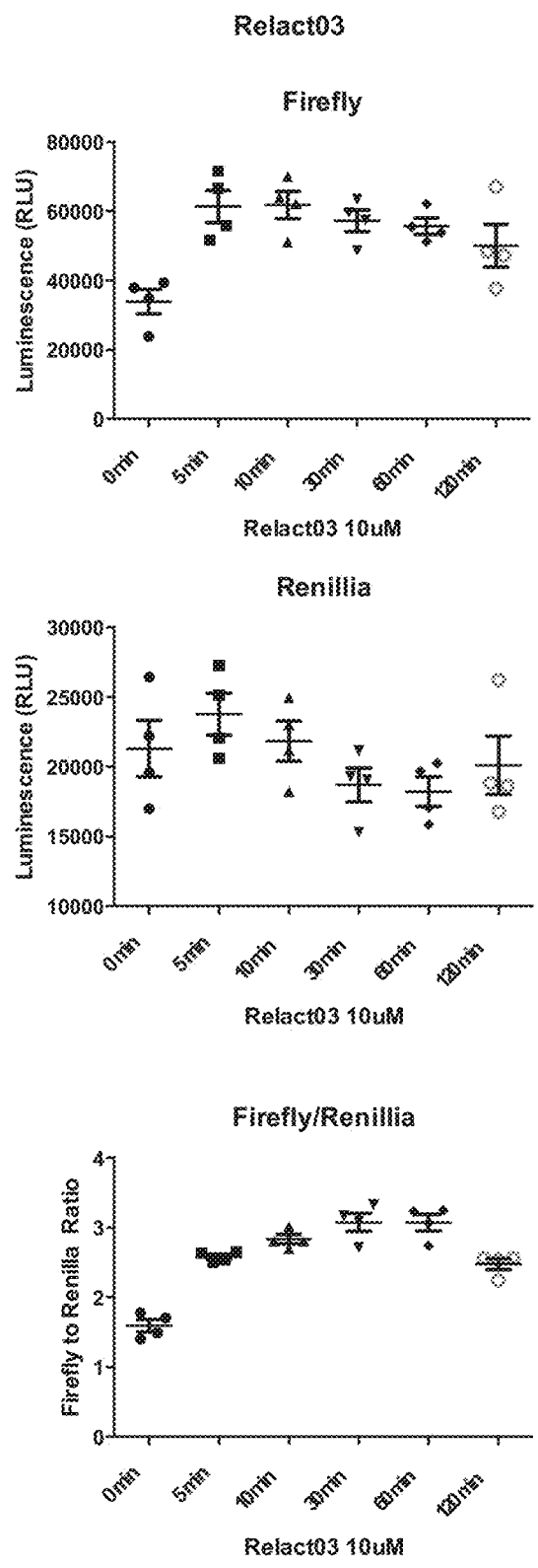

Each of Relact02, Relact03, Relact04, and Relact05 showed a dose response m the ApoER2 luciferase assay (FIG. 4A, FIG. 4B, FIG. 4C, FIG. 4D). Relact02 and Relact03 show a time course at the optimum concentration (FIG. 5A, FIG. 5B).

Example 2

Further Studies with Relact02

Figure 1B:
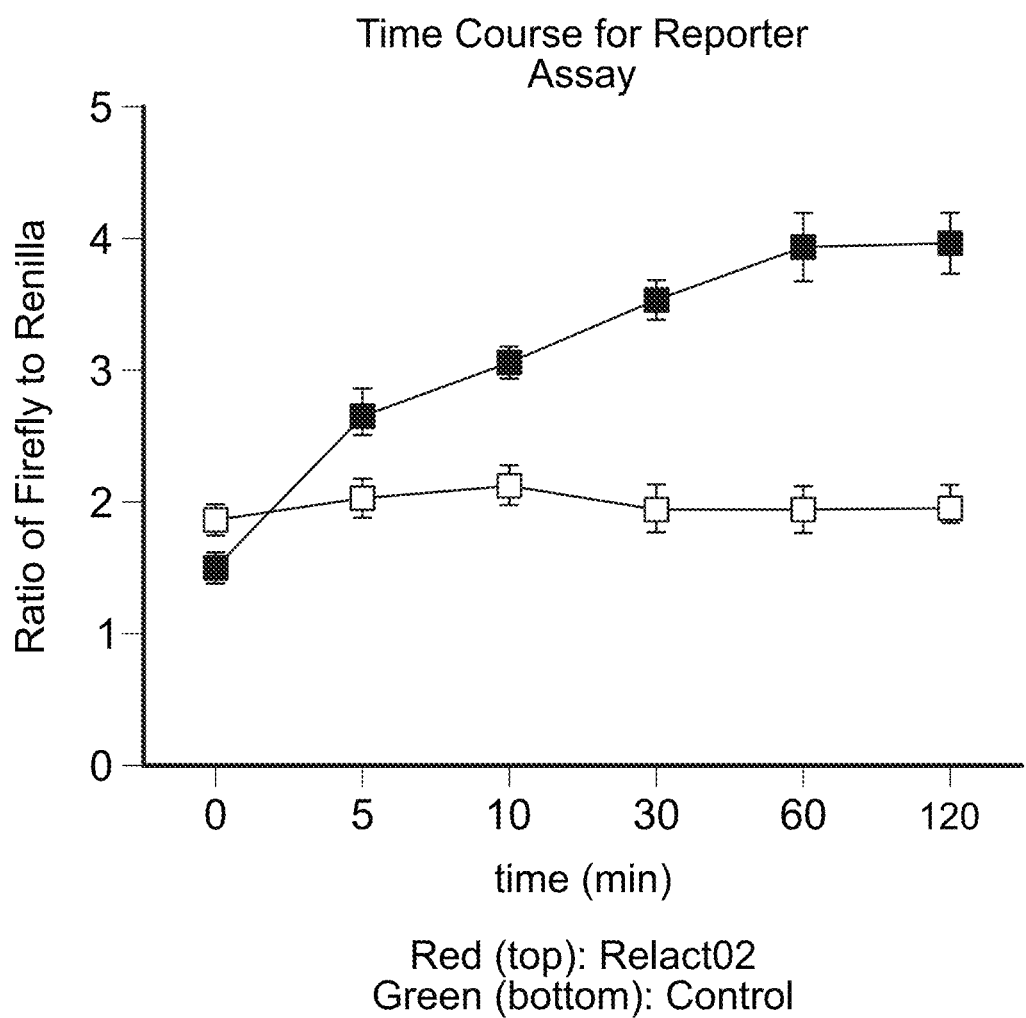
FIG. 1B is a time course for the luciferase assay comparing Relact02 and control.
Figure 1C:
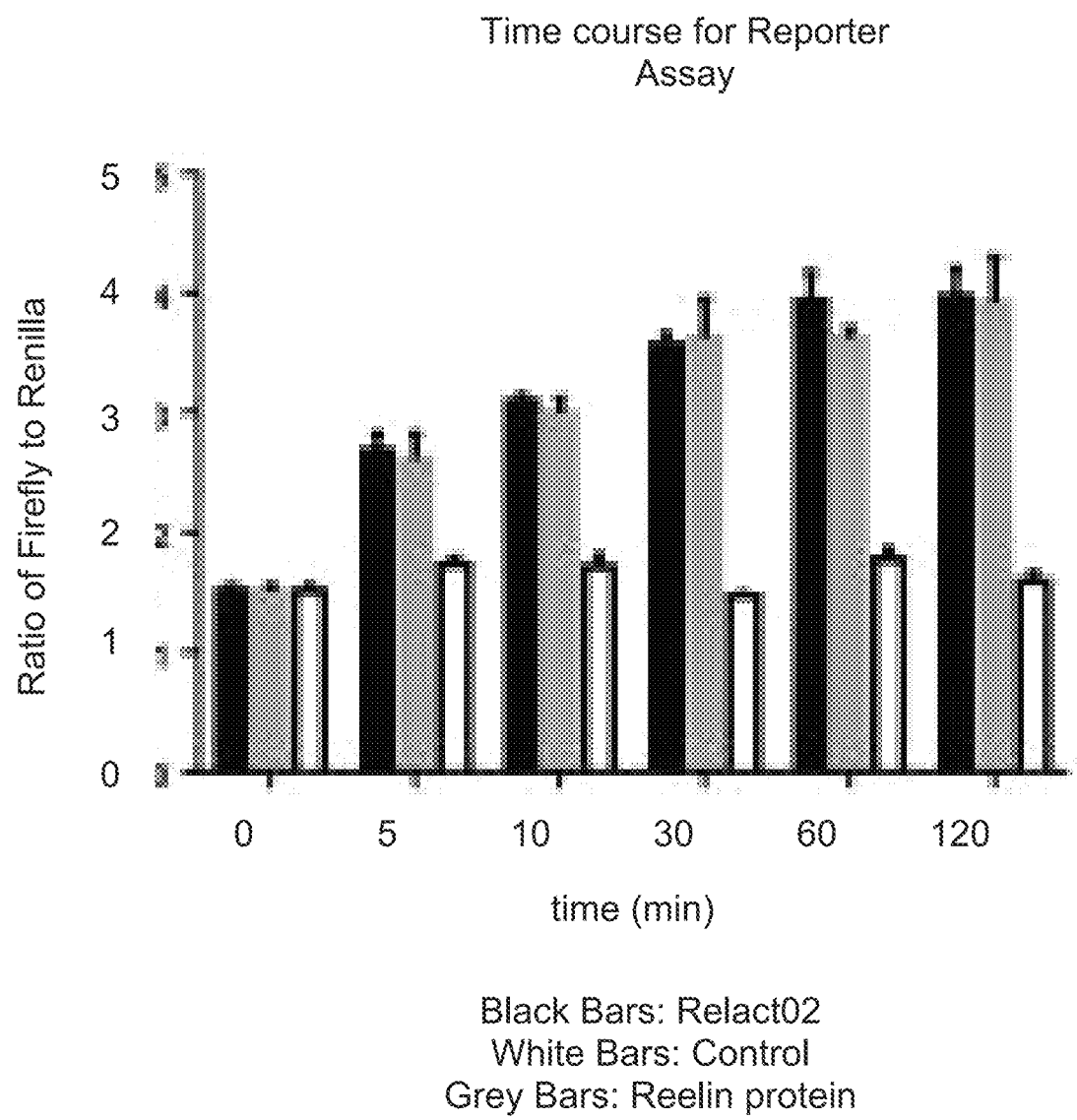
FIG. 1C is a time course for the luciferase assay comparing Relact02, Reelin, and control.
Figure 2:
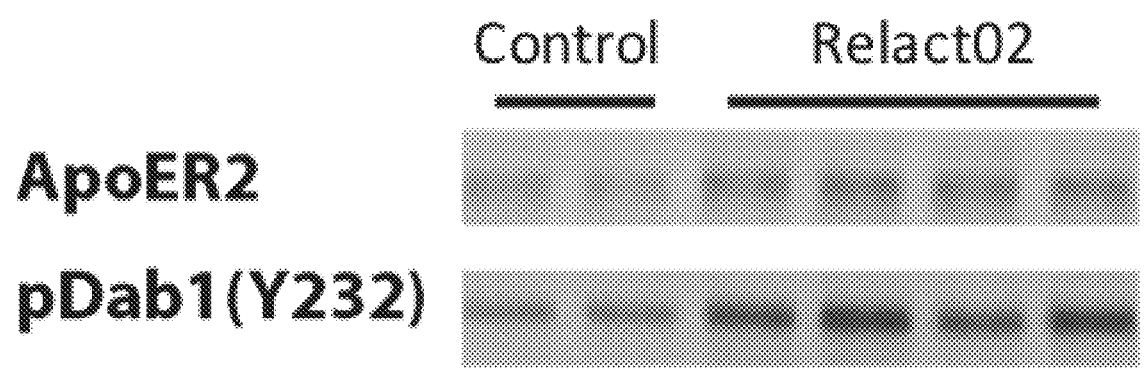
FIG. 2 is gel showing expression of ApoER2 and phosphorylation of DAB-1 in primary neuronal cell cultures upon administration of Relact02 or control.

Relact02 was tested for inducing dimerization of ApoER2 using luciferase as a reporter. Shown in FIG. 1A is a dose response curve assessing luciferase activity. Activity was determined by dimerization of two ApoER2 receptors fused with a luciferase enzyme reporter at the N- or C-terminal region. The control was a compound with structure similar to but different from Relact02. Shown in FIG. 1B is a time course for the luciferase assay using 5 μM of Relact02 or control molecule. Shown in FIG. 1C is a time course using 5 μM Relact02 alone (black bars) or in the presence of the Reelin protein (gray bars). Relact02 induced dimerization of ApoER2 independently of Reelin To confirm this was not simply an artifact showing positive results in our ApoER2 luciferase assay. Relact02 was administered to neuronal primary cell cultures. Primary neuronal cell cultures were treated with 5 μM of control E02 or Relact02 for 1 hour. Treated cultures were probed for an increase in ApoER2 expression, which is an indication of ApoER2 activation and internalization, as well probing for DAB-1 phosphorylation. As shown in FIG. 2, the results indicated Dab-1 phosphorylation and up regulation of ApoER2 recycling with Relact02, which demonstrated specific activation of the Reelin pathway by Relact02. These biochemical changes can only occur through ApoER2 activation and dimerization. Relact02 Induced Dab-1 phosphorylation and up regulation of ApoER2 recycling independently of the Reelin protein.

Example 3

Culture Cell Signaling Assay

Figure 6A:
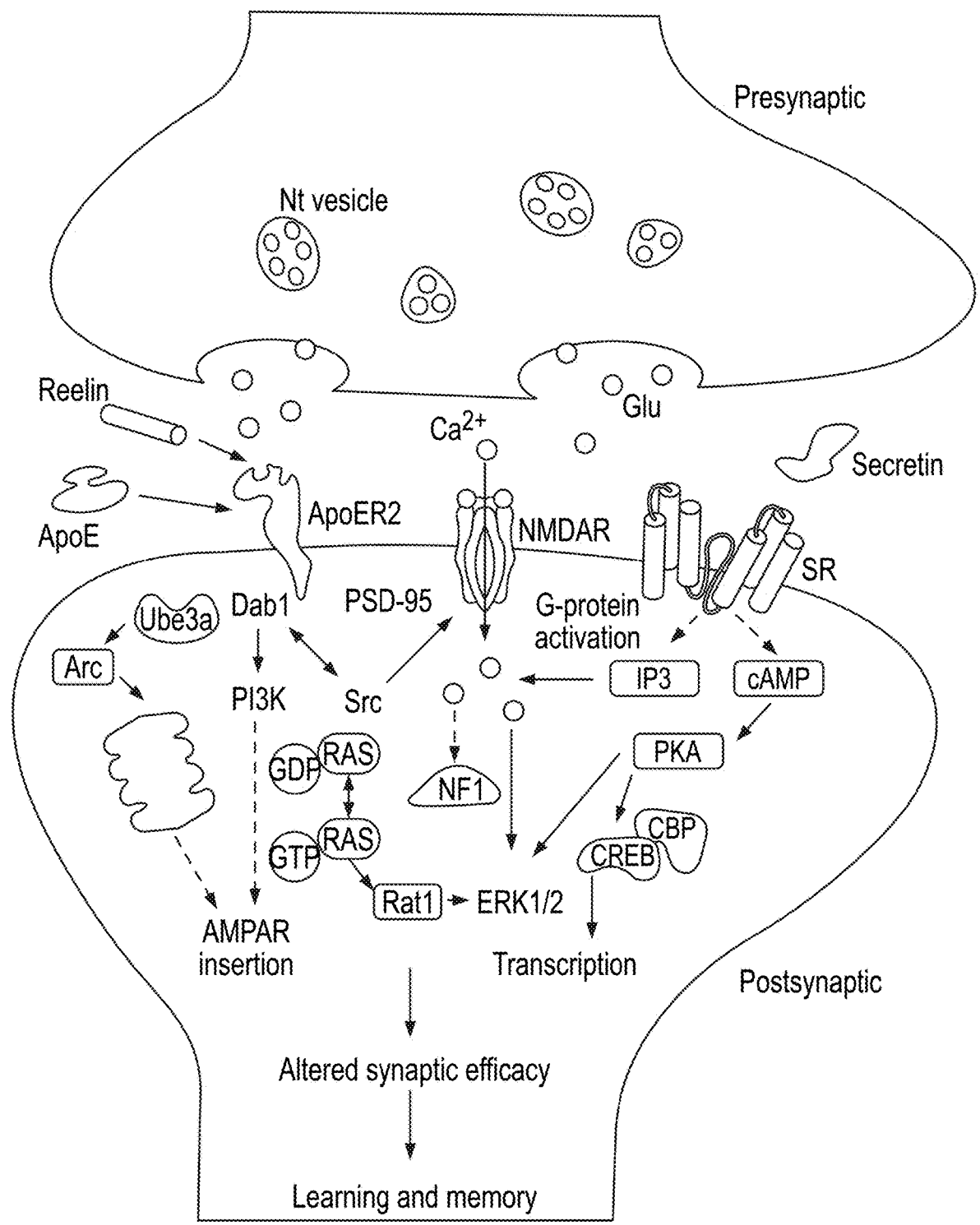
FIG. 6A is a schematic diagram showing how Reelin signaling can modify synaptic function through the activation of downstream effectors ERK and AKT (through PI3K), with the legend in FIG. 6B.
Figure 6B:
Figure 6B:
Figure 6B:
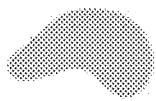
Figure 6B:
Figure 6B:
Figure 6B:
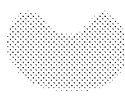
Figure 7A:
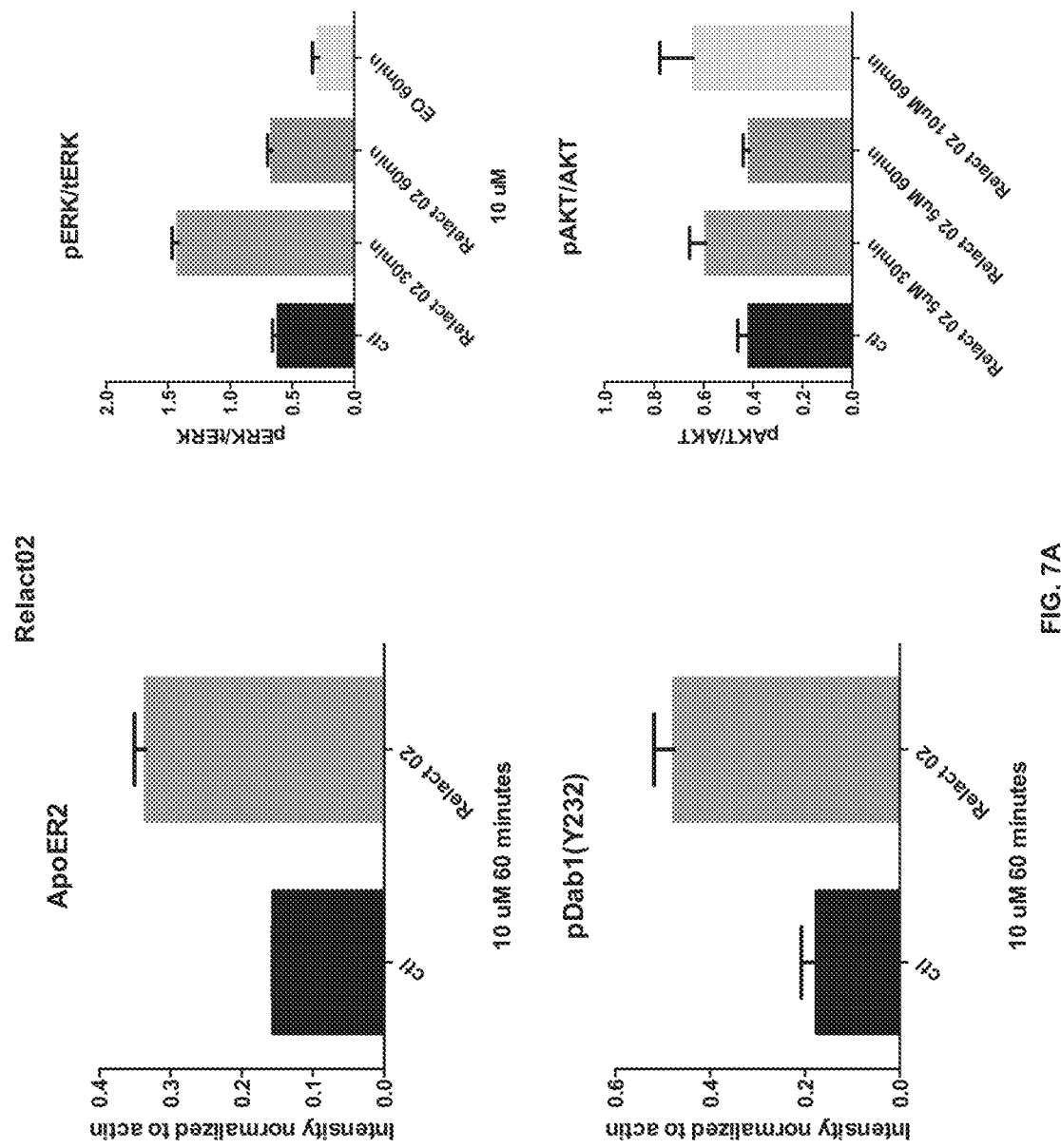
FIG. 7A, FIG. 7B, FIG. 7C, and FIG. 7D are graphs showing in vitro activation of Reelin signaling pathways with Relact02 (FIG. 7A). Relact03 (FIG. 7B). Relact04 (FIG. 7C), and Relact05 (FIG. 7D).
Figure 7B:
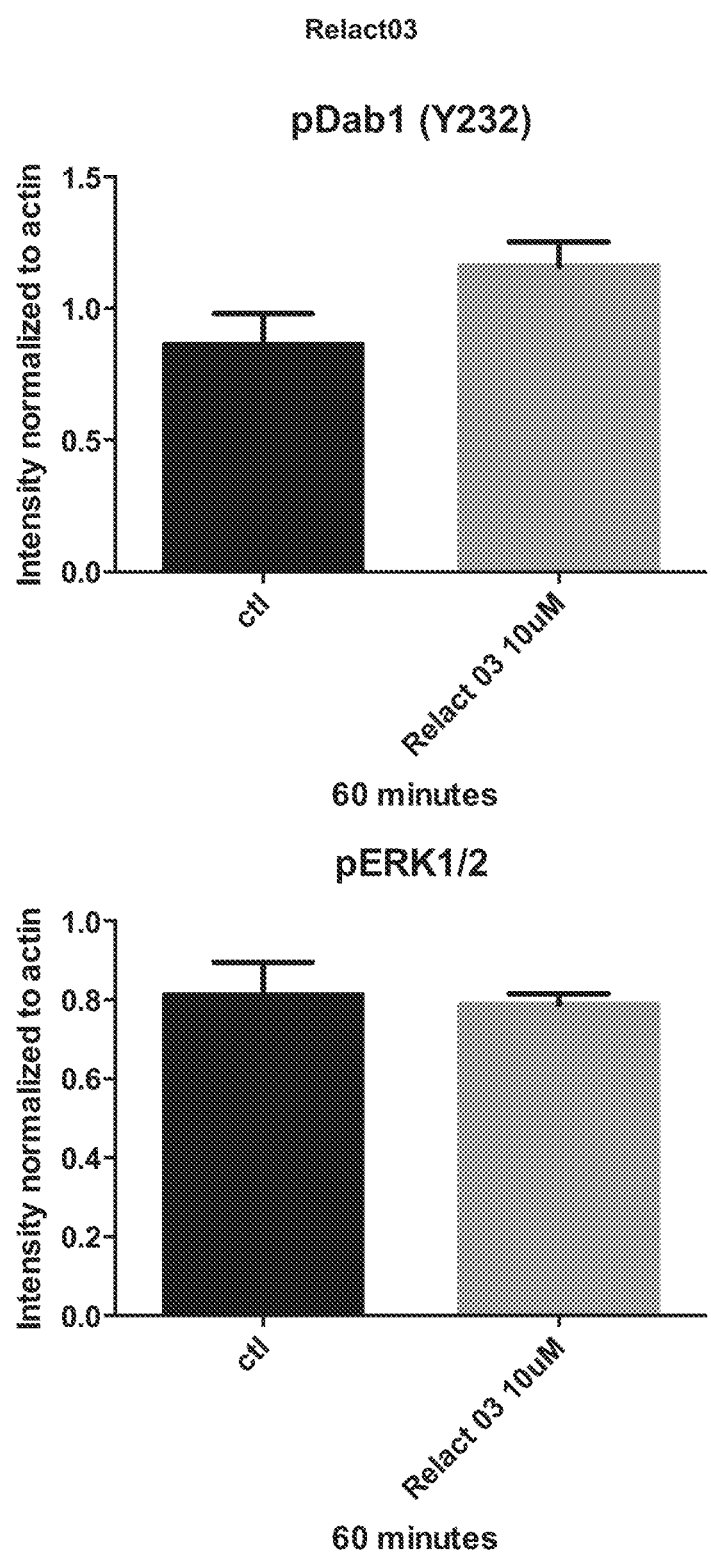
Figure 7C:
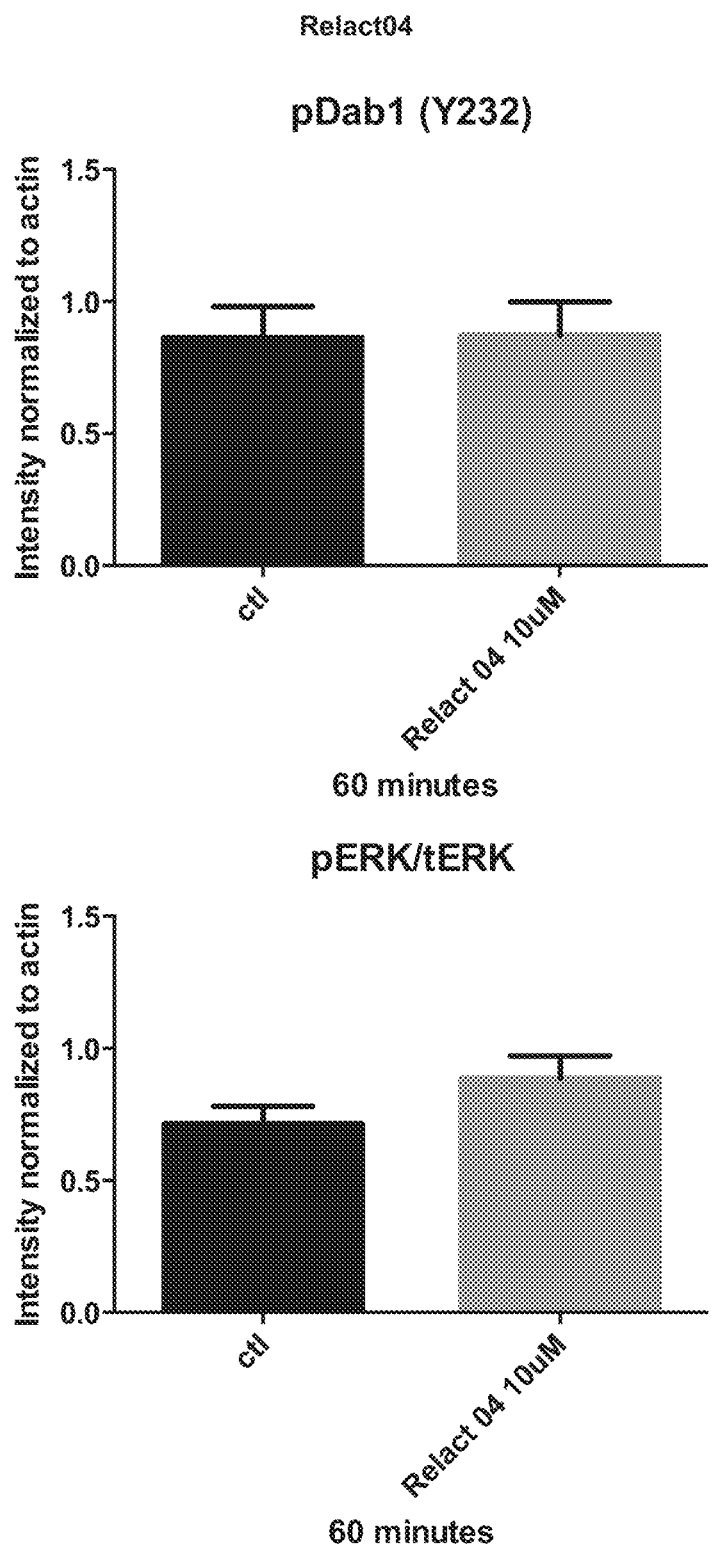
Figure 7D:
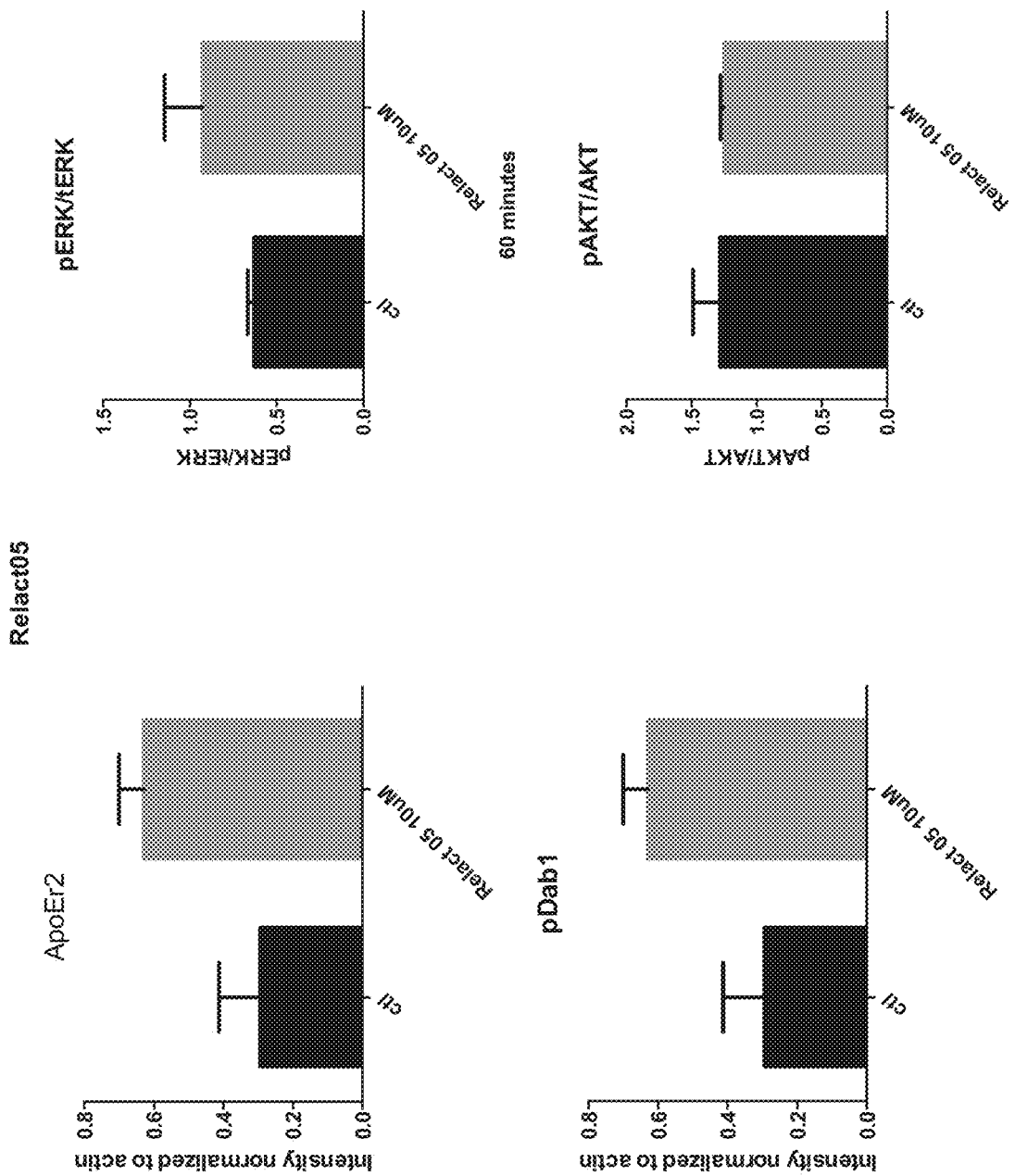

With the ApoER2 luciferase assay, the amount of Receptor clustering can be seen. However, it is unknown whether clustering can occur with an unaltered ApoER2 receptor. ApoER2 is highly expressed in the CNS, and primary neuronal cultures show intact AppoER2 and the downstream intracellular adapter protein Dab-1 (FIG. 6A, FIG. B). There is also a confirmed signal transduction system in cultures linking Dab-1 activation to ERK and AKT, as well as changings in ApoER2 expression. To test the ability of certain compounds (Relact02, Relact03, Relact04, and Relact05) to activate an in vitro Reelin signaling system, we applied the compounds to mouse neuronal primary cultures for 2 hours and performed Western analysis to determine the activation of downstream Reelin receptor signaling pathways (Dab1, ERK, and AKT) (FIG. 7A, FIG. 7B, FIG. 7C, FIG. 7D)

Example 4

Studies in Hippocampal Slices

Figure 8:
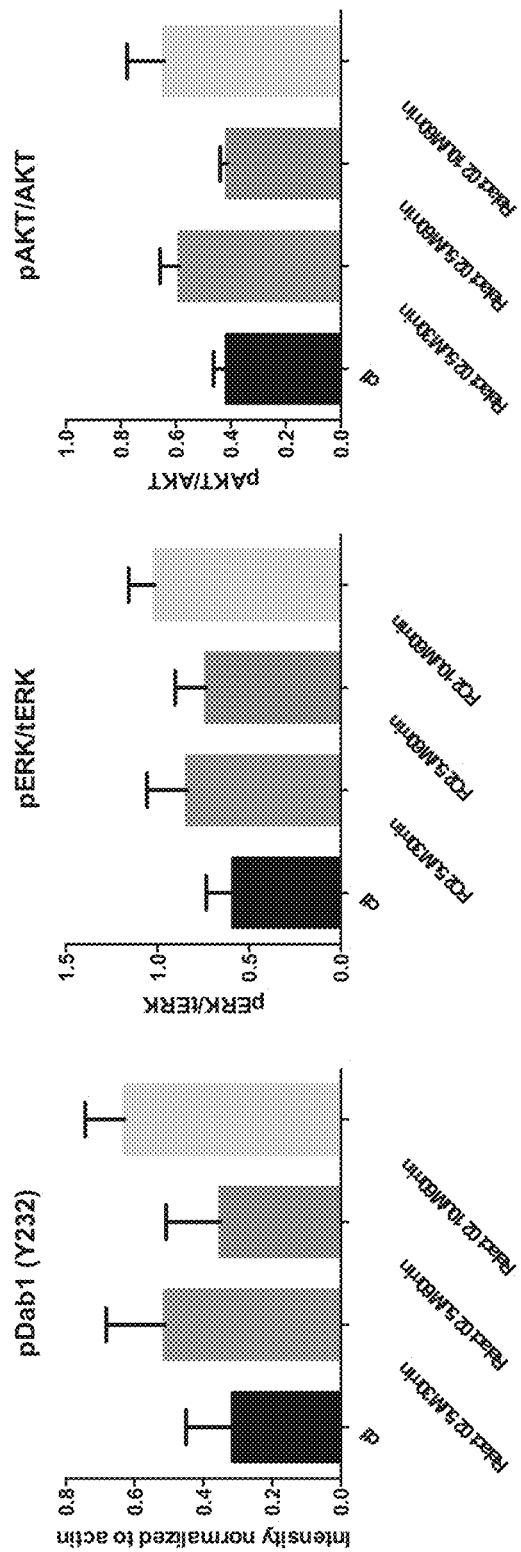
FIG. 8 are graphs showing the effect of Relact02 on levels of pDab1, pERK/tERK, and pAKT/AKT in adult hippocampal slices. These tests represent a greater neuronal complexity and indicate an ability to signal in an in vim system.

The biochemical activity of Relact02 in hippocampal slices as a result of induced Reelin was examined. The results are shown in FIG. 8.

Other compounds (Relact03, Relact04, and Relact05) will be tested similarly.

Example 5

Control Studies

We sought to determine if analogs of Relact02 and Relact05 could impart similar ApoER2 clustering using the ApoER2 luciferase assay. The analogs were identified by ChemBridge (San Diego, Calif.) as the most similar compounds to Relact02 and are shown below with information in TABLE 1.

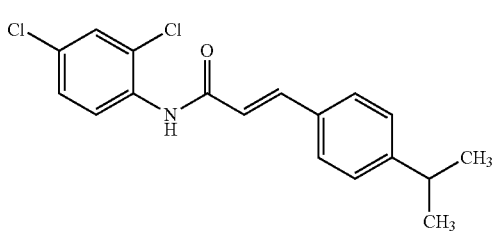

(2)

N-(2,4-dichlorophenyl)-3-(4-isopropylphenyl)acrylamide
$C_{18}H_{17}Cl_2NO$
Compound ID 6847970

-continued (3)

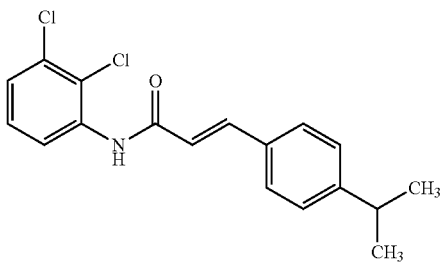

N-(2,3-dichlorophenyl)-3-(4-isopropylphenyl)acrylamide
$C_{18}H_{17}Cl_2NO$
Compound ID 5278590

(4)

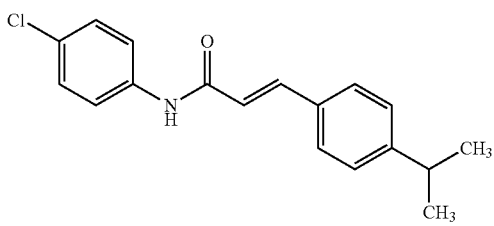

N-(4-chlorophenyl)-3-(4-isopropylphenyl)acrylamide
$C_{18}H_{18}ClNO$
Compound ID 5263004

(5)

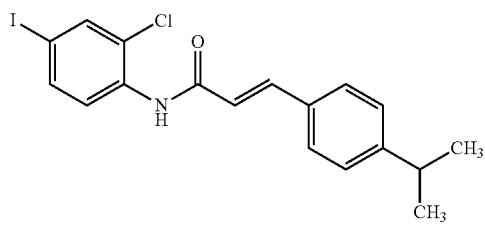

N-(2-chloro-4-iodophenyl)-3-(4-isopropylphenyl)acrylamide
$C_{18}H_{17}ClINO$
Compound ID 6918349

TABLE 1

| Compound ID | MW | Formula | LogP | LogS W | Rotatable Bonds | tPSA | hDon | hAcc | Form |
|---|---|---|---|---|---|---|---|---|---|
| (2) 6847970 | 334 | $C_{18}H_{17}Cl_2NO$ | 6.01 | −6.77 | 3 | 29.1 | 1 | 1 | Solid |
| (3) 5278590 | 334 | $C_{18}H_{17}Cl_2NO$ | 5.88 | −6.66 | 3 | 29.1 | 1 | 1 | Solid |
| (4) 5263004 | 300 | $C_{18}H_{18}ClNO$ | 6.06 | −6.56 | 3 | 29.1 | 1 | 1 | Solid |
| (5) 6918349 | 426 | $C_{18}H_{17}ClINO$ | 6.42 | −7.79 | 3 | 29.1 | 1 | 1 | Solid |

Figure 9A:
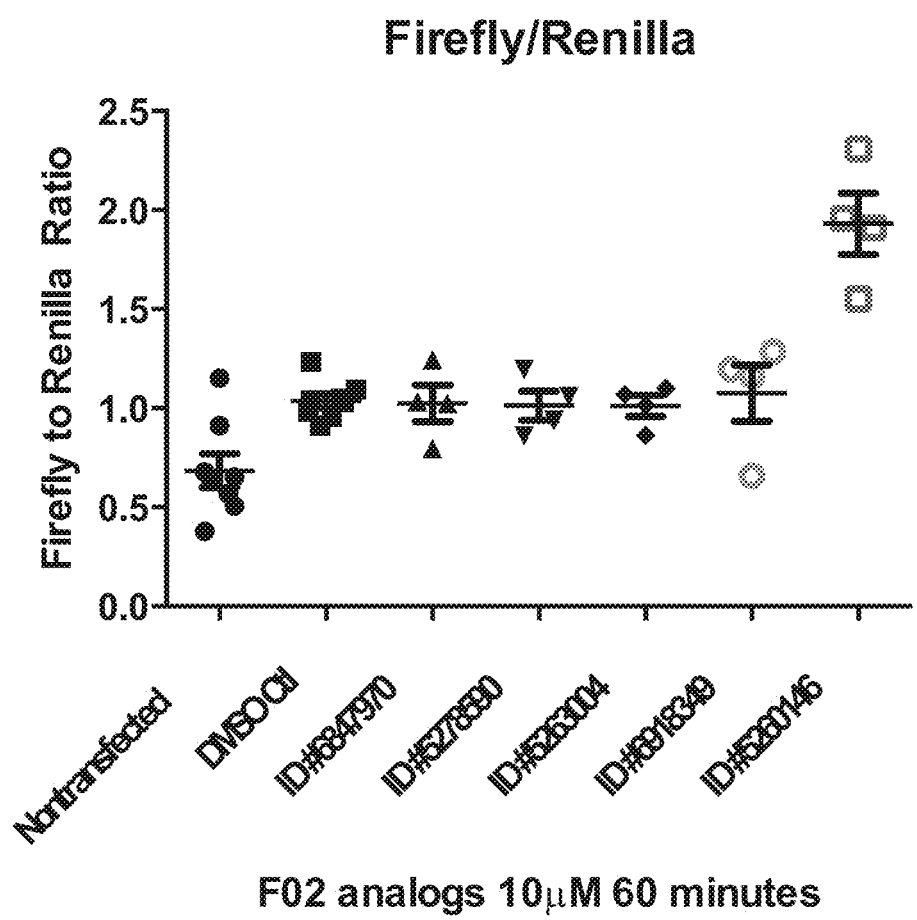
FIG. 9A is a graph of Firefly/Renilla fluorescence for Relact02 analogs according to the ApoER2 luciferase assay at 10 μM analog concentration and 60 minutes.
Figure 9B:
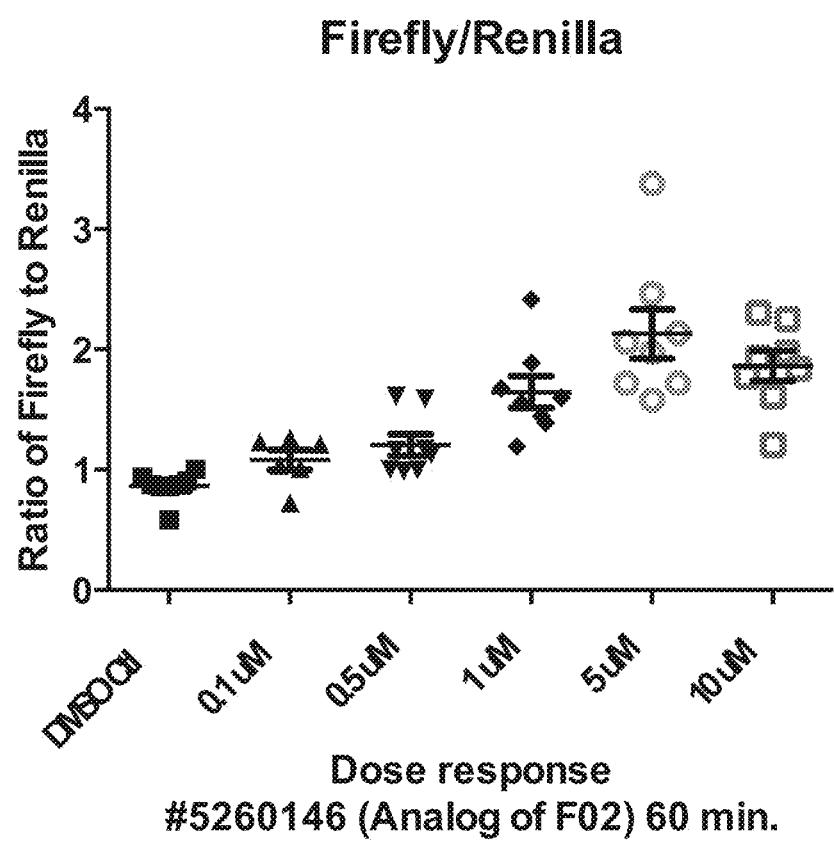
FIG. 9B is a graph of Firefly/Renilla fluorescence for various concentrations of a Relact02 analog (Compound ID 5260146) according to the ApoER2 luciferase assay

It was found that at a 10 μM concentration, the analogs—each of compounds (2), (3), (4), and (5)—did not show changes in firefly/renilla ratios in the ApoER2 luciferase assay (FIG. 9A, FIG. 9B).

The foregoing description of the specific aspects will so fully reveal the general nature of the invention that others can, by applying knowledge within the skill of the art, readily modify and/or adapt for various applications such specific aspects, without undue experimentation, without departing from the general concept of the present disclosure. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary aspects, but should be defined only in accordance with the following claims and their equivalents.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

For reasons of completeness, various aspects of the invention are set out in the following numbered clauses:

Clause 1 A method of treating a disease or disorder in a subject in need thereof, the method comprising administering to the subject an agonist of a lipoprotein receptor.

Clause 2. A method of improving cognitive function in a subject in need thereof, the method comprising administering to the subject an agonist of a lipoprotein receptor.

Clause 3. A method of increasing dendritic spine density in a subject in need thereof, the method comprising administering to the subject an agonist of a lipoprotein receptor.

Clause 4. A method of improving associative learning in a subject in need thereof, the method comprising administering to the subject an agonist of a lipoprotein receptor.

Clause 5. A method of improving spatial learning in a subject in need thereof, the method comprising administering to the subject an agonist of a lipoprotein receptor.

Clause 6. A method of improving long-term potentiation of neurons in a subject in need thereof, the method comprising administering to the subject an agonist of a lipoprotein receptor Clause 7. The method of any one of clauses 1-6, wherein the lipoprotein receptor is selected from ApoER2 and VLDLR Clause 8. The method of clause 1, wherein the disease or disorder is of the central nervous system.

Clause 9. The method of clause 8, wherein the disease or disorder is a developmental disorder, a cognitive disorder, a degenerative disorder, a neuropsychiatric disorder, or brain injury.

Clause 10. The method of clause 9, wherein the developmental disorder is Lissecephaly.

Clause 11 The method of clause 9, wherein the cognitive disorder is selected from Angelman Syndrome and schizophrenia.

Clause 12. The method of clause 9, wherein the degenerative disorder is Alzheimer's disease.

Clause 13. The method of clause 9, wherein the neuropsychiatric disorder is selected from schizophrenia and bipolar disorder.

Clause 14. The method of clause 9, wherein the brain injury is traumatic brain injury (TBI).

Clause 15. The method of clause 8, wherein the disease or disorder is selected from Lissecephaly, fragile X syndrome, William's syndrome, Rett syndrome, Down's syndrome, Angelman syndrome, autism, ischemia, hypoxia, Alzheimers disease, Reelin deficiency, schizophrenia, bipolar disorder, neurodegeneration, traumatic brain injury, mental retardation, dementia, bipolar disorder, and stroke.

Clause 16. A method of treating a central nervous system disease or disorder by activating the Reelin signaling system in a subject in need thereof, the method comprising administering to the subject an effective amount of a small molecule agonist of a lipoprotein receptor.

Clause 17. The method of any one of clauses 1-16, wherein the agonist comprises a compound according to Formula I':

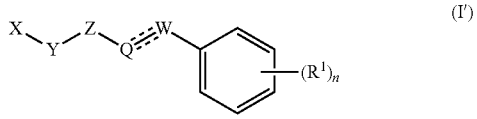

(I')

or a pharmaceutically acceptable salt thereof, wherein each $R^1$ is independently hydrogen, halogen, hydroxyl, alkoxyl, or alkyl; n is an integer from 0 to 5; W is C, CH, CH$_2$, or O; Q is C, CH, CH$_2$, N, or NH; Z is C=O, NH, or CH$_2$; Y is C=O, NH, or CH$_2$, or Z and Y may together form a bicyclic ring; and X is cycloalkyl, cycloalkenyl, cycloalkynyl, heterocycyl, aryl, or heteroaryl, and may be unsubstituted or substituted with $(R^2)_m$, wherein each $R^2$ is independently hydrogen, halogen, hydroxyl, alkoxyl, or alkyl, and m is an integer from 0 to 5;

or Formula I:

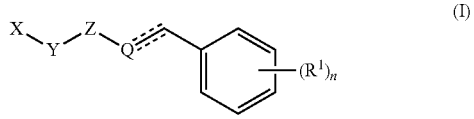

(I)

or a pharmaceutically acceptable salt thereof, wherein each $R^1$ is independently hydrogen, halogen, hydroxyl, alkoxyl, or alkyl; n is an integer from 0 to 5; Q is C, CH, CH$_2$, N, or NH; Z is C=O, NH, or CH$_2$; Y is C=O, NH, or CH$_2$, or Z and Y may together form a bicyclic ring; and X is cycloalkyl, cycloakenyl, cycloakynyl, heterocyclyl, aryl, or heteroaryl, and may be unsubstituted or substituted with $(R^2)_m$, wherein each $R^2$ is independently hydrogen, halogen, hydroxyl, alkoxyl, or alkyl, and m is an integer from 0 to 5;

or Formula II:

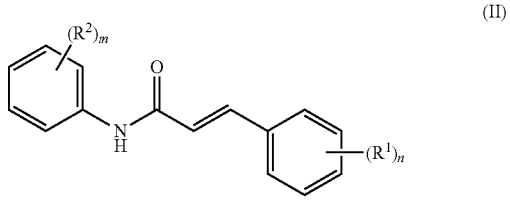

(II)

or a pharmaceutically acceptable salt thereof, wherein each $R^1$ is independently hydrogen, halogen, hydroxyl, alkoxyl, or alkyl; n is an integer from 0 to 5; each $R^2$ is independently hydrogen, halogen, hydroxyl, alkoxyl or alkyl; and m is an integer from 0 to 5;

or Formula III:

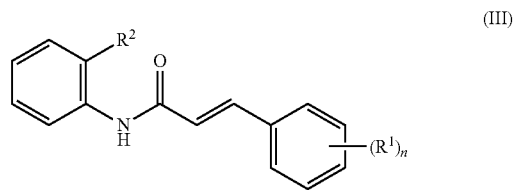

(III)

or a pharmaceutically acceptable salt thereof, wherein each $R^1$ is independently hydrogen, halogen, hydroxyl, alkoxyl, or alkyl; n is an integer from 0 to 5; and $R^2$ is hydrogen, halogen hydroxyl, alkoxyl, or alkyl.

Clause 18. A method of activating a lipoprotein receptor in a subject in need thereof, the method comprising administering to the subject a compound according to Formula I':

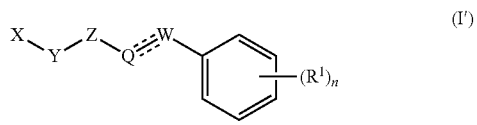

(I')

or a pharmaceutically acceptable salt thereof, wherein each $R^1$ is independently hydrogen, halogen, hydroxyl, alkoxyl, or alkyl; n is an integer from 0 to 5; W is C, CH, CH$_2$, or O, Q is C, CH, CH$_2$, N, or NH; Z is C=O, NH, or CH$_2$; Y is C=O, NH, or CH$_2$, or Z and Y may together form a bicyclic ring, and X is cycloalkyl, cycloalkenyl, cycloalkynyl, heterocyclyl, aryl, or heteroaryl, and may be unsubstituted or substituted with $(R^2)_m$, wherein each $R^2$ is independently hydrogen, halogen, hydroxyl, alkoxyl, or alkyl, and m is an integer from 0 to 5;

or Formula I:

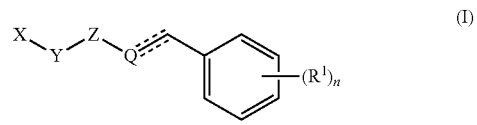

(I)

or a pharmaceutically acceptable salt thereof, wherein each $R^1$ is independently hydrogen, halogen, hydroxyl, alkoxyl, or alkyl; n is an integer from 0 to 5; Q is C, CH, CH$_2$, N, or NH; Z is C=O, NH, or CH$_2$; Y is C=O, NH, or CH$_2$, or Z and Y may together form a bicyclic ring; and X is cycloalkyl, cycloalkenyl, cycloalkynyl, heterocycyl, aryl, or heteroaryl, and may be unsubstituted or substituted with $(R^2)_m$, wherein each $R^2$ is independently hydrogen, halogen, hydroxyl, alkoxyl, or alkyl, and m is an integer from 0 to 5;

or Formula II:

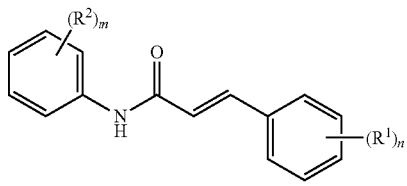

or a pharmaceutically acceptable salt thereof; wherein each $R^1$ is independently hydrogen, halogen, hydroxyl, alkoxyl, or alkyl; n is an integer from 0 to 5; each $R^2$ is independently hydrogen, halogen, hydroxyl, alkoxyl, or alkyl; and m is an integer from 0 to 5;
or Formula III:

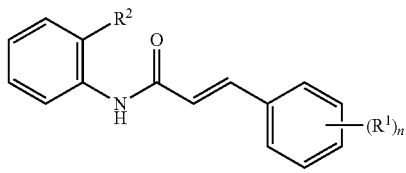

or a pharmaceutically acceptable salt thereof, wherein each $R^1$ is independently hydrogen, halogen, hydroxyl, alkoxyl, or alkyl; n is an integer from 0 to 5; and $R^2$ is hydrogen, halogen, hydroxyl, alkoxyl, or alkyl.

Clause 19. The method of clause 18, wherein the lipoprotein receptor is selected from ApoER2 and VLDLR.

Clause 20. An agonist of ApoER2 or VLDLR, wherein the agonist is a compound according to Formula I':

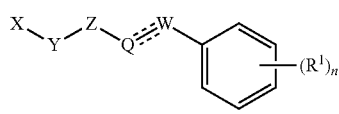

or a pharmaceutically acceptable salt thereof, wherein each $R^1$ is independently hydrogen, halogen, hydroxyl, alkoxyl, or alkyl; n is an integer from 0 to 5; W is C, CH, $CH_2$, or O; Q is C, CH, $CH_2$, N, or NH; Z is C=O, NH, or $CH_2$; Y is C=O, NH, or $CH_2$, or Z and Y may together form a bicyclic ring; and X is cycloalkyl, cycloalkenyl, cycloalkynyl, heterocycyl, aryl, or heteroaryl, and may be unsubstituted or substituted with $(R^2)_m$, wherein each $R^2$ is independently hydrogen, halogen, hydroxyl, alkoxyl, or alkyl, and m is an integer from 0 to 5;
or Formula I:

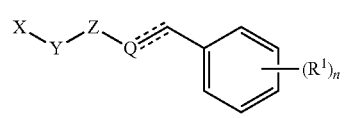

or a pharmaceutically acceptable salt thereof, wherein each $R^1$ is independently hydrogen, halogen, hydroxyl, alkoxyl, or alkyl; n is an integer from 0 to 5; Q is C, CH, $CH_2$, N, or NH; Z is C=O, NH, or $CH_2$; Y is C=O, NH, or $CH_2$, or Z and Y may together form a bicyclic ring; and X is cycloakyl, cycloalkenyl, cycloalkynyl, heterocyclyl, aryl, or heteroaryl, and may be unsubstituted or substituted with $(R^2)_m$, wherein each $R^2$ is independently hydrogen, halogen, hydroxyl, alkoxyl, or alkyl, and m is an integer from 0 to 5;
or Formula II:

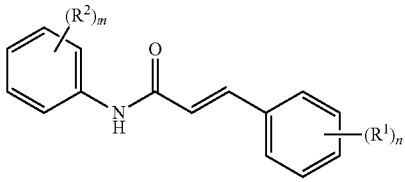

or a pharmaceutically acceptable salt thereof, wherein each $R^1$ is independently hydrogen, halogen, hydroxyl, alkoxyl, or alkyl, n is an integer from 0 to 5; each $R^2$ is independently hydrogen, halogen hydroxyl, alkoxyl, or alkyl; and m is an integer from 0 to 5;
or Formula III:

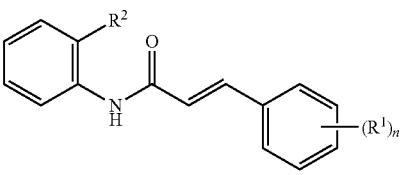

or a pharmaceutically acceptable salt thereof, wherein each $R^1$ is independently hydrogen, halogen, hydroxyl, alkoxyl, or alkyl; n is an integer from 0 to 5; and $R^2$ is hydrogen, halogen, hydroxyl, alkoxyl, or alkyl Clause 21. A compound according to Formula I':

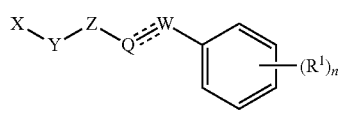

or a pharmaceutically acceptable salt thereof, wherein each $R^1$ is independently hydrogen, halogen, hydroxyl, alkoxyl, or alkyl; n is an integer from 0 to 5; W is C, CH, $CH_2$, or O; Q is C, CH, $CH_2$, N, or NH; Z is C=O, NH, or $CH_2$; Y is C=O, NH, or $CH_2$, or Z and Y may together form a bicyclic ring; and X is cycloalkyl, cycloalkenyl, cycloalkynyl, heterocyclyl, aryl, or heteroaryl, and may be unsubstituted or substituted with $(R^2)_m$, wherein each $R^2$ is independently hydrogen, halogen, hydroxyl, alkoxyl, or alkyl, and m is an integer from 0 to 5;
or Formula I:

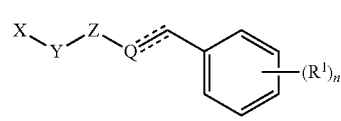

or a pharmaceutically acceptable salt thereof, wherein each $R^1$ is independently hydrogen, halogen, hydroxyl, alkoxyl, or alkyl; n is an integer from 0 to 5; Q is C, CH, $CH_2$, N, or NH. Z is C=O, NH, or $CH_2$; Y is C=O, NH, or $CH_2$, or Z and Y may together form a bicyclic ring; and X is cycloalkyl, cycloalkenyl, cycloalkynyl, heterocyclyl, aryl, or heteroaryl, and may be unsubstituted or substituted with $(R^2)_m$, wherein each $R^2$ is independently hydrogen, halogen, hydroxyl, alkoxyl, or alkyl, and m is an integer from 0 to 5;

or Formula II

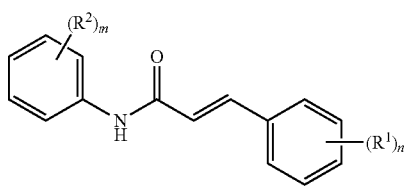

or a pharmaceutically acceptable salt thereof, wherein each $R^1$ is independently hydrogen, halogen, hydroxyl, alkoxyl, or alkyl, n is an integer from 0 to 5; each $R^2$ is independently hydrogen, halogen, hydroxyl, alkoxyl, or alkyl; and m is an integer from 0 to 5;

or Formula III:

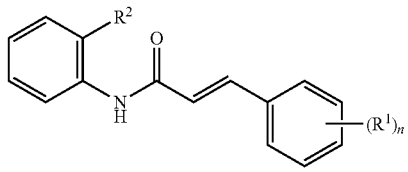

or a pharmaceutically acceptable salt thereof, wherein each $R^1$ is independently hydrogen, halogen, hydroxyl, alkoxyl, or alkyl; n is an integer from 0 to 5; and $R^2$ is hydrogen, halogen, hydroxyl, alkoxyl, or alkyl.

Clause 22. A pharmaceutical composition comprising the compound of clause 21.

Clause 23. The composition of clause 22, further comprising a carrier for oral, intranasal, intravaginal, transdermal, intravenous, intraarterial, intratumoral, intraperitoneal, or topical administration.

Clause 24. The method or agonist or compound of any one of clauses 17-23, wherein the agonist or compound is of Formula I', and wherein R1 is methoxy, OH, or isopropyl Clause 25. The method or agonist or compound of any one of clauses 17-23, wherein the agonist or compound is of Formula I', and wherein Z and Y together form a heteroaryl ring.

Clause 26. The method or agonist or compound of any one of clauses 17-23, wherein the agonist or compound is of Formula I', and wherein Z and Y together form benzimidazole.

Clause 27. The method or agonist or compound of any one of clauses 17-23, wherein the agonist or compound is of Formula I', and wherein X is phenyl substituted with (R2)m.

Clause 28. The method or agonist or compound of clause 27, wherein at least one R2 is methyl.

Clause 29. The method or agonist or compound of clause 27, wherein at least one R2 is Cl or I.

Clause 30. The method or agonist or compound of any one of clauses 17-23, wherein the agonist or compound is of Formula I, and wherein R1 is methoxy, OH, or isopropyl.

Clause 31. The method or agonist or compound of any one of clauses 17-23, wherein the agonist or compound is of Formula I, and wherein Z and Y together form a heteroaryl ring.

Clause 32. The method or agonist or compound of any one of clauses 17-23, wherein the agonist or compound is of Formula I, and wherein Z and Y together form benzimidazole.

Clause 33. The method or agonist or compound of any one of clauses 17-23, wherein the agonist or compound is of Formula I, and wherein X is phenyl substituted with (R2)m.

Clause 34. The method or agonist or compound of clause 33, wherein at least one R2 is methyl.

Clause 35. The method or agonist or compound of clause 33, wherein at least one R2 is Cl or I.

Clause 36. The method or agonist or compound of any one of clauses 17-23, wherein the agonist or compound is of Formula II, and wherein R1 is C1-4 alkyl Clause 37. The method or agonist or compound of clause 36, wherein R1 is methyl, ethyl, or isopropyl Clause 38. The method or agonist or compound or composition of any one of clauses 17-23, wherein the agonist or compound is of Formula II, and wherein R2 is Cl or I.

Clause 39. The method or agonist or compound or composition of any one of clauses 17-23, wherein the agonist or compound is of Formula I', wherein R1 is Cl, n is 2, W is O, Q is CH2, Z is C=O, Y is NH, and X is phenyl substituted with (R2)m, wherein R2 is Cl and m is 1

Clause 40. The method or agonist or compound or composition of any one of clauses 17-23, wherein the agonist or compound is of Formula III, wherein R1 is methyl, ethyl, or isopropyl.

Clause 41. The method or agonist or compound or composition of any one of clauses 17-23, wherein the agonist or compound is of Formula III, wherein R1 is isopropyl.

Clause 42. The method or agonist or compound or composition of any one of clauses 40-41, wherein n is 1 or 2.

Clause 43. The method or agonist or compound or composition of any one of clauses 17-23, wherein the agonist or compound is of Formula III, wherein R2 is Cl.

Clause 44. The method or agonist or compound or composition of any one of clauses 17-23, wherein the agonist or compound is of Formula III, wherein R2 is Cl, R1 is isopropyl, and n is 1.

Clause 45. The method or agonist or compound or composition of any one of clauses 17-23, wherein the agonist or compound is selected from the following:

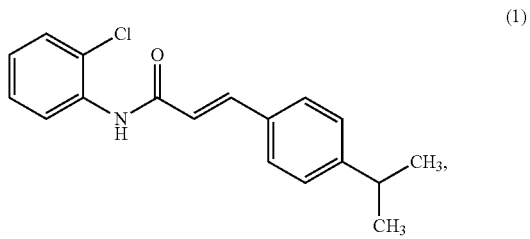 [SMILES: CC(C)c1ccc(/C=C/C(=O)Nc2ccccc2Cl)cc1]

-continued (2)
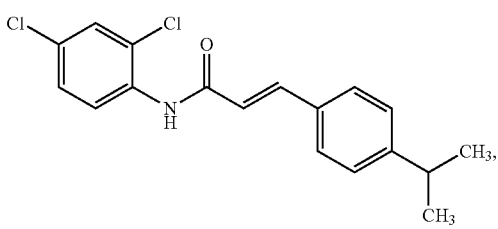

(3)
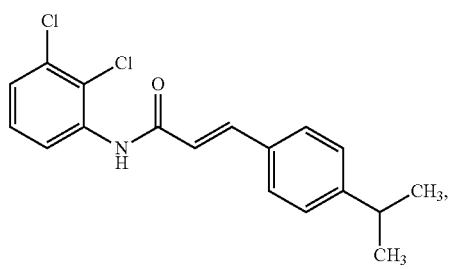

(4)
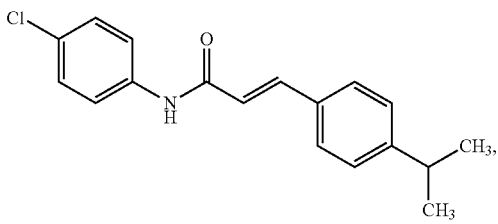

(5)
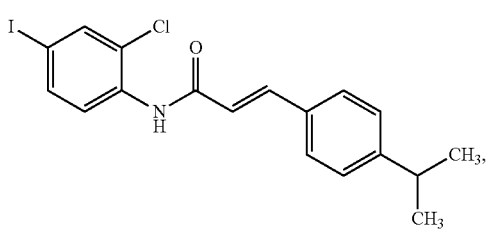

(6)
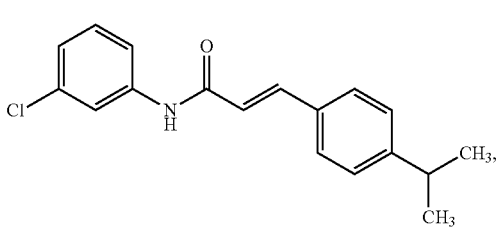

(7)
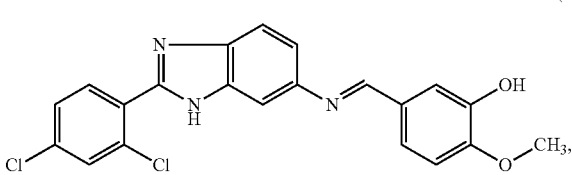

(8)
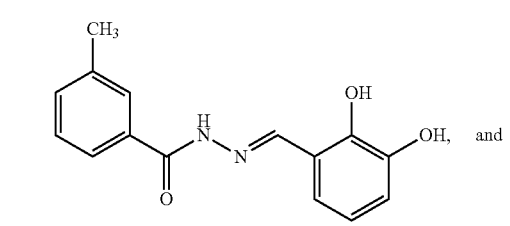

-continued (9)
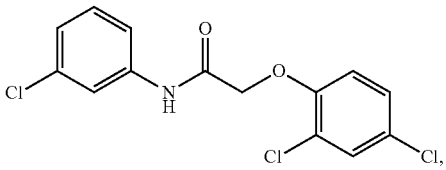

or a pharmaceutically acceptable salt thereof.

The invention claimed is:

1. A method of treating a disease or disorder of the central nervous system is a selected from a developmental disorder, a cognitive disorder, a degenerative disorder, a neuropsychiatric disorder, or traumatic brain injury in a subject in need thereof comprising, administering to the subject an effective amount of an agonist of a lipoprotein receptor, wherein the lipoprotein receptor is selected from ApoER2 and VLDLR, thereby improving cognitive function, increasing dendritic spine density, improving associative learning, improving special learning, or improving long-term potentiation of neurons, and wherein the agonist is a compound of Formula I:

(I)
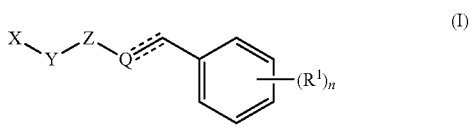

or a pharmaceutically acceptable salt thereof, wherein each $R^1$ is independently hydrogen, halogen, hydroxyl, alkoxyl, or alkyl;

n is an integer from 0 to 5;

Q is C, CH, $CH_2$, N, or NH;

Z is C=O, NH, or $CH_2$;

Y is C=O, NH, or $CH_2$, or Z and Y may together form a bicyclic ring; and

X is cycloalkyl, cycloalkenyl, cycloalkynyl, heterocyclyl, aryl, or heteroaryl, and may be unsubstituted or substituted with $(R^2)_m$, wherein each $R^2$ is independently hydrogen, halogen, hydroxyl, alkoxyl, or alkyl, and m is an integer from 0 to 5.

2. The method of claim 1, wherein the disease or disorder of the central nervous system is the result of a Reelin deficiency.

3. The method of claim 2, wherein the disease or disorder of the central nervous system is selected from Lissencephaly, fragile X syndrome, William's syndrome, Rett syndrome, Down's syndrome, Angelman syndrome, autism, ischemia, hypoxia, Alzheimer's disease, schizophrenia, bipolar disorder, neurodegeneration, traumatic brain injury, mental retardation, dementia, bipolar disorder, and stroke.

4. The method of claim 1, wherein the lipoprotein receptor is ApoER2.

5. The method of claim 1, wherein the lipoprotein receptor is VLDLR.

6. The method of claim 1, wherein the compound is:

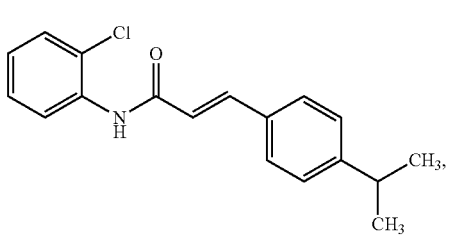

(1)

or a pharmaceutically acceptable salt thereof.

7. The method of claim 1, wherein the compound is:

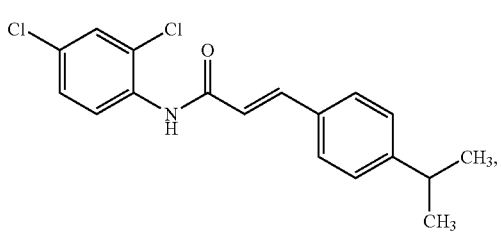

(2)

or a pharmaceutically acceptable salt thereof.

8. The method of claim 1, wherein the compound is:

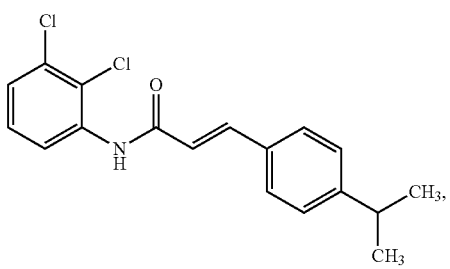

(3)

or a pharmaceutically acceptable salt thereof.

9. The method of claim 1, wherein the compound is:

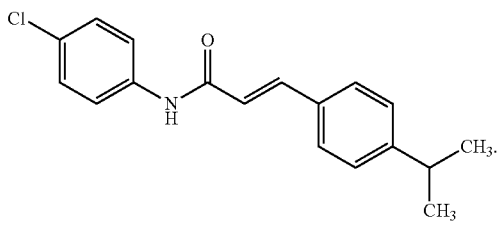

(4)

or a pharmaceutically acceptable salt thereof.

10. The method of claim 1, wherein the compound is:

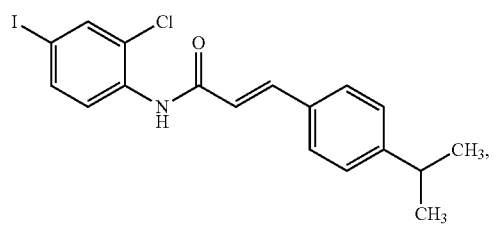

(5)

or a pharmaceutically acceptable salt thereof.

11. The method of claim 1, wherein the compound is:

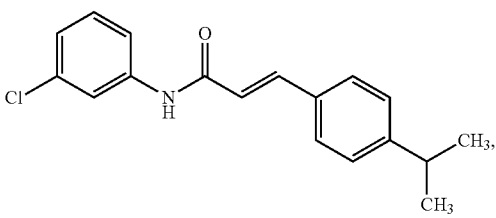

(6)

or a pharmaceutically acceptable salt thereof.

12. The method of claim 1, wherein the compound is:

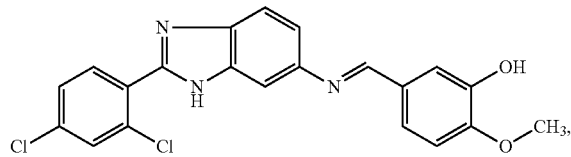

(7)

or a pharmaceutically acceptable salt thereof.

13. The method of claim 1, wherein the compound is:

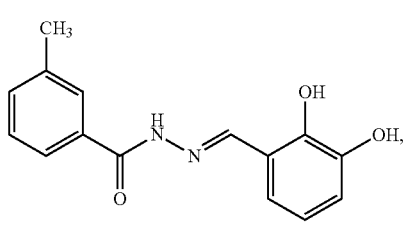

(8)

or a pharmaceutically acceptable salt thereof.

14. The method of claim 1, wherein the agonist is a compound of Formula II:

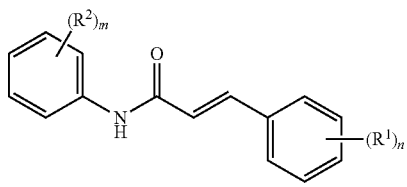

or a pharmaceutically acceptable salt thereof,
wherein each $R^1$ is independently hydrogen, halogen, hydroxyl, alkoxyl, or alkyl;
n is an integer from 0 to 5; and
each $R^2$ is independently hydrogen, halogen, hydroxyl, alkoxyl, or alkyl; and
m is an integer from 0 to 5.

15. The method of claim 1, wherein the agonist is a compound of Formula III:

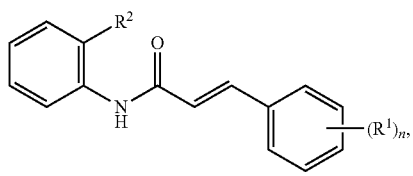

or a pharmaceutically acceptable salt thereof,
wherein each $R^1$ is independently hydrogen, halogen, hydroxyl, alkoxyl, or alkyl;
n is an integer from 0 to 5; and
each $R^2$ is independently hydrogen, halogen, hydroxyl, alkoxyl, or alkyl.

\* \* \* \* \*